(12) United States Patent
Winkler et al.

(10) Patent No.: US 7,736,906 B2
(45) Date of Patent: Jun. 15, 2010

(54) COMBINATORIAL STRATEGIES FOR POLYMER SYNTHESIS

(75) Inventors: James L. Winkler, Sunnyvale, CA (US); Stephen P. A. Fodor, Palo Alto, CA (US); Christopher J. Buchko, Ann Arbor, MI (US); Debra A. Ross, Fremont, CA (US); Lois Aldwin, San Mateo, CA (US); Douglas N. Modlin, Palo Alto, CA (US)

(73) Assignee: Affymetrix, Inc., Santa Clara, CA (US)

( * ) Notice: Subject to any disclaimer, the term of this patent is extended or adjusted under 35 U.S.C. 154(b) by 901 days.

(21) Appl. No.: 10/172,939

(22) Filed: Jun. 17, 2002

(65) Prior Publication Data

US 2004/0092032 A1    May 13, 2004

Related U.S. Application Data

(63) Continuation of application No. 09/579,982, filed on May 26, 2000, which is a continuation of application No. 09/498,554, filed on Feb. 4, 2000, now Pat. No. 6,943,034, which is a continuation of application No. 09/129,463, filed on Aug. 4, 1998, now Pat. No. 6,040,193, which is a continuation of application No. 08/426,202, filed on Apr. 21, 1995, now Pat. No. 6,136,269, which is a continuation of application No. 07/980,523, filed on Nov. 20, 1992, now Pat. No. 5,677,195, which is a continuation-in-part of application No. 07/874,849, filed on Apr. 24, 1992, now Pat. No. 5,412,087, and a continuation-in-part of application No. 07/796,243, filed on Nov. 22, 1991, now Pat. No. 5,384,261.

(51) Int. Cl.
    *G01N 1/28* (2006.01)
(52) U.S. Cl. .................. 436/174; 436/178; 436/183
(58) Field of Classification Search .................. 436/174, 436/178, 180, 183
    See application file for complete search history.

(56) References Cited

U.S. PATENT DOCUMENTS

| | | |
|---|---|---|
| 3,077,780 A | 2/1963 | Takatsy |
| 3,281,860 A | 10/1966 | Adams et al. |
| 3,490,879 A | 1/1970 | Urban |
| 3,615,240 A | 10/1971 | Sanz |
| 3,730,844 A | 5/1973 | Gilham et al. |
| 3,848,998 A | 11/1974 | Yonekura et al. |
| 3,915,704 A | 10/1975 | Limburg et al. |
| 4,016,855 A | 4/1977 | Mimata |
| 4,031,197 A | 6/1977 | Marinkovich |
| 4,121,222 A | 10/1978 | Diebold et al. |
| 4,162,896 A | 7/1979 | Hosli |
| 4,166,457 A | 9/1979 | Jacobsen et al. |
| 4,216,245 A | 8/1980 | Johnson |
| 4,282,287 A | 8/1981 | Giese |
| 4,325,913 A | 4/1982 | Wardlaw |
| 4,327,073 A | 4/1982 | Huang |
| 4,340,390 A | 7/1982 | Collins et al. |
| 4,378,333 A | 3/1983 | Laipply |
| 4,392,362 A | 7/1983 | Little |
| 4,483,920 A | 11/1984 | Gillespie et al. |
| 4,533,682 A | 8/1985 | Tortorello et al. |
| 4,537,861 A | 8/1985 | Elings et al. |
| 4,542,102 A | 9/1985 | Dattagupta et al. |
| 4,562,157 A | 12/1985 | Lowe et al. |
| 4,584,277 A | 4/1986 | Ullman |
| 4,586,546 A | 5/1986 | Mezei et al. |
| 4,588,682 A | 5/1986 | Groet et al. |
| 4,591,570 A | 5/1986 | Chang |
| 4,596,697 A | 6/1986 | Ballato |
| 4,598,049 A | 7/1986 | Zelinka et al. |
| 4,607,526 A | 8/1986 | Bachenheimer et al. |
| 4,613,566 A | 9/1986 | Potter |
| 4,631,211 A | 12/1986 | Houghten |
| 4,656,007 A | 4/1987 | Douchy et al. |
| 4,656,127 A | 4/1987 | Mundy |
| 4,657,867 A * | 4/1987 | Guhl et al. ............... 435/305.3 |
| 4,668,476 A | 5/1987 | Bridgham et al. |
| 4,675,301 A | 6/1987 | Charneski et al. |
| 4,677,054 A | 6/1987 | White et al. |
| 4,681,870 A | 7/1987 | Balint, Jr. et al. |

(Continued)

FOREIGN PATENT DOCUMENTS

| | | |
|---|---|---|
| CA | 1284931 C | 6/1991 |
| EP | 063 810 B1 | 3/1986 |
| EP | 228 075 A2 | 7/1987 |
| EP | 268 237 A2 | 5/1988 |
| EP | 130 523 B1 | 6/1988 |

(Continued)

OTHER PUBLICATIONS http://www.seradyn.com/micro/particle.aspx?id=3.*
http://www.ingentaconnect.com/content/els/09565663/2004/00000019/00000007/art00275.*
http://www.nanoterra/surface_chemistry.asp.*
http://www.ncbi.mlm.nih.gov/enrez/query.fcgi?cmd=Retrieve&db=PubMed&list_uids=8041.*
Hazum et al., "A Photocleavable Protecting Group for the Thiol Function of Cysteine," *Proc. 16th European Peptide Sym.*, pp. 105-110 (1987).

(Continued)

Primary Examiner—Jan M Ludlow
(74) Attorney, Agent, or Firm—Thomas J. Siepmann

(57) ABSTRACT

A method and device for forming large arrays of polymers on a substrate (401). According to a preferred aspect of the invention, the substrate is contacted by a channel block (407) having channels (409) therein. Selected reagents are delivered through the channels, the substrate is rotated by a rotating stage (403), and the process is repeated to form arrays of polymers on the substrate. The method may be combined with light-directed methodologies.

10 Claims, 21 Drawing Sheets

U.S. PATENT DOCUMENTS

| | | | |
|---|---|---|---|
| 4,689,405 A | 8/1987 | Frank et al. | |
| 4,704,256 A | 11/1987 | Hood et al. | |
| 4,704,353 A | 11/1987 | Humphries et al. | |
| 4,711,955 A | 12/1987 | Ward et al. | |
| 4,713,326 A | 12/1987 | Dattagupta et al. | |
| 4,715,413 A | 12/1987 | Backlund et al. | |
| 4,728,502 A | 3/1988 | Hamill | |
| 4,728,591 A | 3/1988 | Clark et al. | |
| 4,731,325 A | 3/1988 | Palva et al. | |
| 4,737,344 A | 4/1988 | Koizumi et al. | |
| 4,738,669 A | 4/1988 | Vlock | |
| 4,746,490 A | 5/1988 | Saneii | |
| 4,755,458 A | 7/1988 | Rabbani et al. | |
| 4,757,437 A | 7/1988 | Nishimura | |
| 4,762,881 A | 8/1988 | Kauer | |
| 4,798,706 A | 1/1989 | Brigati | |
| 4,811,062 A | 3/1989 | Tabata et al. | |
| 4,818,492 A | 4/1989 | Shimizu | |
| 4,820,630 A | 4/1989 | Taub | |
| 4,828,801 A | 5/1989 | Lombardy wife Alric et al. | |
| 4,833,092 A | 5/1989 | Geysen | |
| 4,834,946 A | 5/1989 | Levin | |
| 4,849,513 A | 7/1989 | Smith et al. | |
| 4,855,225 A | 8/1989 | Fung et al. | |
| 4,861,420 A | 8/1989 | Knutti et al. | |
| 4,861,866 A | 8/1989 | Durrum et al. | |
| 4,868,103 A | 9/1989 | Stavrianopoulos et al. | |
| 4,874,500 A | 10/1989 | Madou et al. | |
| 4,877,745 A | 10/1989 | Hayes et al. | |
| 4,886,741 A | 12/1989 | Schwartz | |
| 4,906,439 A | 3/1990 | Grenner | |
| 4,921,805 A | 5/1990 | Gebeyehu et al. | |
| 4,923,901 A | 5/1990 | Koester et al. | |
| 4,925,785 A | 5/1990 | Wang et al. | |
| 4,937,188 A | 6/1990 | Giese et al. | |
| 4,937,593 A | 6/1990 | Prats | |
| 4,943,032 A | 7/1990 | Zdeblick | |
| 4,944,922 A | 7/1990 | Hayashi | |
| 4,948,565 A | 8/1990 | Bemis et al. | |
| 4,966,646 A | 10/1990 | Zdeblick | |
| 4,973,493 A | 11/1990 | Guire | |
| 4,978,507 A | 12/1990 | Levin | |
| 4,981,783 A | 1/1991 | Augenlicht | |
| 4,987,065 A | 1/1991 | Stavrianopoulos et al. | |
| 4,988,617 A | 1/1991 | Landegren et al. | |
| 4,994,373 A | 2/1991 | Stavrianopoulos et al. | |
| 4,997,521 A | 3/1991 | Howe et al. | |
| 5,002,867 A | 3/1991 | Macevicz | |
| 5,011,770 A | 4/1991 | Kung et al. | |
| 5,026,773 A | 6/1991 | Steel | |
| 5,026,840 A | 6/1991 | Dattagupta et al. | |
| 5,028,525 A | 7/1991 | Gray et al. | |
| 5,037,882 A | 8/1991 | Steel | |
| 5,041,266 A * | 8/1991 | Fox | 422/102 |
| 5,043,265 A | 8/1991 | Tanke et al. | |
| 5,053,454 A | 10/1991 | Judd | |
| 5,059,398 A | 10/1991 | Kenney | |
| 5,063,081 A | 11/1991 | Cozzette et al. | |
| 5,077,085 A | 12/1991 | Schnur et al. | |
| 5,077,210 A | 12/1991 | Eigler et al. | |
| 5,079,600 A | 1/1992 | Schnur et al. | |
| 5,082,830 A | 1/1992 | Brakel et al. | |
| 5,094,594 A | 3/1992 | Brennan | |
| 5,100,626 A | 3/1992 | Levin | |
| 5,100,777 A | 3/1992 | Chang | |
| 5,110,555 A | 5/1992 | Moore et al. | |
| 5,143,849 A | 9/1992 | Barry et al. | |
| 5,143,854 A | 9/1992 | Pirrung et al. | |
| 5,171,695 A | 12/1992 | Ekins | |
| 5,175,209 A | 12/1992 | Beattie et al. | |
| 5,200,051 A | 4/1993 | Cozzette et al. | |
| 5,202,231 A | 4/1993 | Drmanac et al. | |
| 5,204,268 A | 4/1993 | Matsumoto | |
| 5,215,882 A | 6/1993 | Bahl et al. | |
| 5,225,326 A | 7/1993 | Bresser et al. | |
| 5,232,829 A | 8/1993 | Longiaru et al. | |
| 5,250,263 A | 10/1993 | Manz | |
| 5,252,743 A | 10/1993 | Barrett et al. | |
| 5,279,558 A | 1/1994 | Kriesel | |
| 5,288,514 A | 2/1994 | Ellman | |
| 5,306,510 A | 4/1994 | Meltzer | |
| 5,310,523 A | 5/1994 | Smethers et al. | |
| 5,310,893 A | 5/1994 | Erlich et al. | |
| 5,324,633 A | 6/1994 | Fodor et al. | |
| 5,338,688 A | 8/1994 | Deeg et al. | |
| 5,348,855 A | 9/1994 | Dattagupta et al. | |
| 5,378,638 A | 1/1995 | Deeg et al. | |
| 5,384,261 A | 1/1995 | Winkler et al. | |
| 5,384,262 A | 1/1995 | Piasio et al. | |
| 5,405,783 A | 4/1995 | Pirrung et al. | |
| 5,412,087 A * | 5/1995 | McGall et al. | 536/24.3 |
| 5,429,807 A | 7/1995 | Matson et al. | |
| 5,432,099 A | 7/1995 | Ekins | |
| 5,436,327 A | 7/1995 | Southern et al. | |
| 5,445,934 A | 8/1995 | Fodor et al. | |
| 5,447,841 A | 9/1995 | Gray et al. | |
| 5,449,754 A | 9/1995 | Nishioka | |
| 5,451,502 A * | 9/1995 | George, Jr. | 435/6 |
| 5,455,008 A | 10/1995 | Earley et al. | |
| 5,465,629 A | 11/1995 | Waylett, Jr. | |
| 5,474,796 A * | 12/1995 | Brennan | 427/2.13 |
| 5,486,452 A | 1/1996 | Gordon et al. | |
| 5,489,507 A | 2/1996 | Chehab | |
| 5,492,806 A | 2/1996 | Drmanac et al. | |
| 5,510,270 A | 4/1996 | Fodor et al. | |
| 5,525,464 A | 6/1996 | Drmanac et al. | |
| 5,532,128 A | 7/1996 | Eggers et al. | |
| 5,545,531 A | 8/1996 | Rava et al. | |
| 5,593,839 A | 1/1997 | Hubbell et al. | |
| 5,631,734 A | 5/1997 | Stern et al. | |
| 5,653,939 A | 8/1997 | Hollis et al. | |
| 5,667,940 A | 9/1997 | Hsue et al. | |
| 5,667,972 A | 9/1997 | Drmanac et al. | |
| 5,670,322 A * | 9/1997 | Eggers et al. | 435/6 |
| 5,677,195 A | 10/1997 | Winkler et al. | |
| 5,695,522 A | 12/1997 | Lemaire, III et al. | |
| 5,695,940 A | 12/1997 | Drmanac et al. | |
| 5,700,637 A | 12/1997 | Southern | |
| 5,744,305 A | 4/1998 | Fodor et al. | |
| 5,770,151 A | 6/1998 | Roach et al. | |
| 5,800,992 A | 9/1998 | Fodor et al. | |
| 5,807,522 A | 9/1998 | Brown et al. | |
| 5,869,237 A | 2/1999 | Ward et al. | |
| 5,885,837 A | 3/1999 | Winkler et al. | |
| 6,040,193 A | 3/2000 | Winkler et al. | |
| 6,096,276 A | 8/2000 | Laursen | |
| 6,136,269 A | 10/2000 | Winkler et al. | |

FOREIGN PATENT DOCUMENTS

| | | |
|---|---|---|
| EP | 281 927 A2 | 9/1988 |
| EP | 328 256 A1 | 8/1989 |
| EP | 337 498 A2 | 10/1989 |
| EP | 392 546 A2 | 10/1990 |
| EP | 425 411 A2 | 5/1991 |
| EP | 173 339 B1 | 1/1992 |
| EP | 171 150 B1 | 3/1992 |
| EP | 237 362 B1 | 3/1992 |
| EP | 185 547 B1 | 6/1992 |
| EP | 304 202 B1 | 7/1992 |
| EP | 260 965 B1 | 11/1992 |
| EP | 232 967 B1 | 4/1993 |
| EP | 235 726 B1 | 5/1993 |
| EP | 373 203 B1 | 8/1994 |

| | | | |
|---|---|---|---|
| EP | 225 807 B1 | 10/1994 |
| EP | 445 915 B1 | 8/1995 |
| GB | 2 156 074 A | 10/1985 |
| GB | 2 233 654 A | 1/1991 |
| JP | 62-254034 A | 11/1987 |
| JP | 63-136002 A | 6/1988 |
| JP | 63-223557 A | 9/1988 |
| WO | 84/03151 A1 | 8/1984 |
| WO | 85/01051 A1 | 3/1985 |
| WO | 86/00991 A1 | 2/1986 |
| WO | 86/06487 A1 | 11/1986 |
| WO | 88/01302 A1 | 2/1988 |
| WO | 89/10977 A1 | 11/1989 |
| WO | 89/11548 A1 | 11/1989 |
| WO | 90/00626 A1 | 1/1990 |
| WO | 90/02605 A1 | 3/1990 |
| WO | 90/03382 A1 | 4/1990 |
| WO | 90/04652 A1 | 5/1990 |
| WO | 90/05746 A1 | 5/1990 |
| WO | 90/05749 A1 | 5/1990 |
| WO | 90/05785 A1 | 5/1990 |
| WO | 90/05789 A1 | 5/1990 |
| WO | 90/07582 A1 | 7/1990 |
| WO | 90/10746 A1 | 9/1990 |
| WO | WO 90/10977 | 9/1990 |
| WO | 90/15070 A1 | 12/1990 |
| WO | 91/00868 A1 | 1/1991 |
| WO | WO 91/02714 | 3/1991 |
| WO | 91/07087 A1 | 5/1991 |
| WO | 91/10746 A1 | 7/1991 |
| WO | 92/10092 A1 | 6/1992 |
| WO | 92/10588 A1 | 6/1992 |
| WO | 93/09668 A1 | 5/1993 |
| WO | 93/17126 A1 | 9/1993 |
| WO | 95/01051 A1 | 1/1995 |
| WO | 97/10365 A1 | 3/1997 |
| YU | P-570-87 | 4/1987 |
| YU | 18617/87-P-570-87 | 2/1988 |

OTHER PUBLICATIONS

Hoeprich, "Total Chemical Synthesis of HIV-1 Protease Using Fmoc/t-butyl Protection Strategy," *Biosystems Reporter*, pp. 3-5, Aug. 1991.
Opposition Brief, Opposition to EP Patent 0 804 731, by Garching Innovation GmbH, Feb. 25, 2000.
Statement of Facts and Arguments, Opposition to EP Patent 0 804 731 by Vysis, Inc., Feb. 25, 2000.
Facts and Arguments, Opposition to EP Patent 0 804 731 by Affymetrix, Inc., Feb. 28, 2000.
Facts and Arguments in Support of Opposition, Opposition to EP Patent 0 804 731 by Andrew Gregory Sheard, Feb. 28, 2000.
Statement of Facts and Arguments, Opposition to EP Patent 0 804 731 by Glaxo Group Limited, Feb. 25, 2000.
Abbott et al., "Manipulation of the Wettability of Surfaces on the 0.1—to 1—Micrometer Scale Through Micromachining and Molecular Self-Assembly," *Science*, 257:1380-1382 (1992).
Anand et al., "A 3.5 genome equivalent multi access YAC library: construction, characterisation, screening and storage," *Nuc. Acids Res.*, 18(8):1951-1956 (1990).
Arnold et al., "A Novel Universal Support for DNA & RNA Synthesis," abstract from *Federation Proceedings*, 43(7): abstract No. 3669 (1984).
Augenlicht et al., "Cloning and Screening of Sequences Expressed in a Mouse Colon Tumor" *Cancer Research*, 42:1088-1093 (1982).
Augenlicht et al., "Expression of Cloned Sequences in Biopsies of Human Colonic Tissue and in Colonic Carcinoma Cells Induced to Differentiate in Vitro," *Cancer Res.*, 47:6017-6021 (1987).
Bains et al, "A Novel Method for Nucleic Acid Sequence Determination," *Theor. Biol.*, 135:303-307 (1988).
Bannwarth et al., "Laboratory Methods, A System for the Simultaneous Chemical synthesis of Different DNA Fragments on Solid-Support," *DNA*, 5(5):413-419 (1986).

Baringa, M., "Will 'DNA Chip' Speed Genome Initiative," *Science*, 253:1489 (1985).
Bartsh et al., "Cloning of mRNA sequences from the human colon: Preliminary characterisation of defined mRNAs in normal and neoplastic tissues" *Br.J.Can.*, 54:791-798 (1986).
Baxendale et al., "The direct screening of cosmid libraries with YAC clones," *Nuc. Acids Res.*, 19(23):6651 (1991).
Beltz et al., "Isolation of Multigene Families and Determination of Homologies by Filler Hybridization Methods," *Methods in Enzymology*, 100:266-285 (1983).
Bernardini et al., "Applications of Piezoelectric Fluid Jetting Devices to Neuroscience Research," *J. Neuroscience Meth.*, 38:81-88 (1991).
Bhatia et al., "New Approach to Producing Patterned Biomolecular Assemblies," *J. Am. Chemical Society*, 114:4432-4433 (1992).
Bhatia et al., "Immobilization of Acetylcholinesterase on Solid Surfaces: Chemistry and Activity," *Sensors and Actuators B*, 3:311-317 (1991).
Boyle et at, "Differential distribution of long and short interspersed element sequences in the mouse genome: Chromosome Karyotyping by fluorescence in situ hybridization," *PNAS*, 87:7757-7761 (1990).
Brock et al., "Rapid fluorescence detection of in situ hybridization with biotinylated bovine herpesvirus-I DNA probes," *J. Veterinary Diagnostic Investigation*, 1:34-38 (1989).
Grant proposal of P.O. Brown, Oct. 1992.
Carrano et al., "A High-Resolution. Fluorescence-Based. Semiautomated Method for DNA Fingerprinting," *Genomics*, 4:129-136 (1989).
Caruthers, M.H., "Gene Synthesis Machines: DNA Chemistry and Its Uses," *Science*, 230:281-285 (1985).
Chehab et al., "Detection of specific DNA sequences by fluorescence amplification: A color complementation assay," *PNAS*, 86:9178-9182 (1989).
Chehab et al., "Detection of sickle cell animia mutation by colour DNA Amplification," *Lancet*, 335:15-17 (1990).
Craig et al., "Ordering of cosmid clones covering the Herpes simplex virus type 1 (HSV-1) genome: a test case for fingerprinting by hybridization," *Nuc. Acid. Res.*, 18(9):2653-2660 (1990).
Dower et al, "The Search for Molecular Diversity (II): Recombinant and Synthetic Randomized Peptide Libraries," from *Annual Reports in Medical Chemistry*, vol. 26, chapter 28, pp. 271-280 (1991).
Drmanac et al., "Laboratory Methods, Reliable Hybridization of Oligonucleotides as Short as Six Nucleotides," *DNA and Cell Biol.*, 9(7):527-534 (1990).
Drmanac et al., "Partial Sequencing by Oligo-Hybridization Concept and Applications in Genome Analysis," 1st Int. Conf. Electrophor.; Supercomp., Hum. Genome pp. 60-74 (1990).
Drmanac et al., "Sequencing by Hybridization: Towards an Automated Sequencing of One Million M13 Clones Arrayed on Membranes," *Electrophoresis*, 13(8):566-573 (1992).
Drmanac et al., "Sequencing by Oligonucleotide Hybridization: A Promising Framework in Decoding of the Genome Program?," 1st Int. Conf. Electrophor., Supercomp., Hum. Genome pp. 47-59 (1990).
Drmanac et al., "Sequencing of Megabase Plus DNA by Hybridization: Theory of the Method," *Genomics*, 4:114-128 (1989).
Ekins et al., "Developments in Immunoassay Methods", *Biochimica Clinics Suppl.*, 1-8; 13 (1989).
Ekins et al., "Fluorescence Spectroscopy and its Application to a New Generation of High Sensitivity, Multi-Microspot, Multianalyte, Immunoassay," *Clin. Chim. Acta*, 194:91-114 (1990).
Ekins et al., "Multianalyte Immunoassay: The Immunological 'Compact Disc' of the future," *J. Clin. Immunoassay*, 13(4):169-181 (1990).
Ekins et al., "High Specific Activity Chemiluminescent and Fluorescent Markers: their Potential Application to High Sensitivity and 'Multi-analyte' Immunoassays," *J. Bioluminescence Chemilumincscence*, 4:59-78 (1989).
Ekins et al., "Development of Microspot Multi-Analyte Ratiometric Immunoassay Using dual Fluorescent-Labelled Antibodies," *Anal. Chemica Acta*, 227:73-96 (1989).
Ekins et al., "Multianalyte Microspot Immunoassay-Microanalytical 'Compact Disk' of the Future," *Clin. Chem.*, 37(11):1955-1967 (1991).

Ekins, R.P., "Multi-Analyte immunoassay*," *J. Pharmaceut. Biomedical Analysis*, 7(2):155-168 (1989).
Evans et al., "Physical mapping of complex genomes by cosmid multiplex analysis," *PNAS*, 86:5030-5034 (1989).
Ezaki et al., "Small-Scale DNA Preparation for Rapid Genetic Identification of *Campylobacter* Species without Radioisotope," *Microbiol. Immunology*, 32(2):141-150 (1988).
Fan et al., "Mapping small DNA sequences by fluorescence in situ hybridization directly on banded metaphase chromosomes," *PNAS*, 87:6223-6227 (1990).
Fodor et al., "Light-directed, Spatially Addressable Parallel Chemical Synthesis," *Science*, 251:767-773 (1991).
Frank et al., "Simultaneous Synthesis and Biological Applications of DNA Fragments: An Efficient and Complete Methodology," *Methods in Enzymology*, 154:221-250 (1987).
Frank et al., "Simultaneous Multiple Peptide Synthesis Under Continuous flow Conditions on Cellulose Paper Discs as Segmental Solid Supports," *Tetrahedron*, 44(19):6031-6040 (1988).
Frank et al., "A new general approach for the simultaneous chemical synthesis of large numbers of oligonucleotides: segmental solid supports," *Nuc. Acids Res.*, 11(13):4365-4377 (1983).
Gergen et al., "Filter replicas and Permanent Collections of Recombinant DNA Plasmids," *Nucleic Acids Res.*, 7(8):2115-2135 (1979).
Geysen et al., "Strategies for epitope analysis using peptide synthesis," *J. Immunol. Methods*, 102:259-274 (1987).
Ghandi, "Lithographic Processes," from *VLSI Fabrication Principles Silicon and Gallium Arsenide*, chapter 10, pp. 535-563 (1983).
Ghosh et al., "Covalent attachment of oligonucleotides to solid supports " *Nuc. Acids Res.*, 15(13):5353-5373 (1987).
Gress et al., "Hybridization fingerprinting of high-density cDNA-library arrays with cDNA pools derived from whole tissues," *Mamm. Genome*, 3:609-619 (1992).
Gummerlock, et al., "RAS Enzyme-Linked Immunoblot Assay Discriminates p21 Species: A Technique to Dissect Gene Family Expression," *Analytival Biochemistry*, 180:158-168 (1989).
Haase et al "Detection of two Viral Genomes in Single Cells by Double-Label Hybridization in Situ and Color Microradioautography," *Science* 227:189-192 (1985).
Hanahan et al., "Plasmid Screening at High Colony Density," *Meth. Enzymology*, 100:333-342 (1983).
Hanahan et al., "Plasmid screening at high colony density," *Gene*, 10:63-67 (1980).
Haridasan et al., "Peptide Synthesis using Photolytically Cleavable 2-Nitrobenzyloxycarbonyl Protecting Group," *Proc. Indian Natn. Sci. Adad.*, 53A(6):717-728 (1987).
Hayes et al., "Application of Ink-Jet Technology to Microelectric Packaging," from Proceedings, ISHM '89 held in Baltimore Maryland, pp. 627-634 (1989).
Hoheisel et al., "Use of high coverage libraries for an integrated analysis of genomic DNA," *Adv. Mol. Gen.*, 4:125-132 (1991).
Hoheisel et al., "Use of High Coverage Reference Libraries of Drosophila melanogaster for Relational Data Analysis " *J. Mol. Biol.*, 220:903-914 (1991).
Hopman et al. "Bi-color detection of two target DNAs by non-radioactive in situ hybridization," *Histochemistry*, 85:1-4 (1986).
Kafatos et al., "Determination of nucleic acid sequence homologies and relative concentrations by a dot hybridization procedure," *Nuc. Acids Res.*, 7(6):1541-1553 (1979).
Kerkof et al., "A Procedure for Making Simultaneous Determinations of the Relative Levels of Gene Transcripts in Tissues or Cells," *Anal. Biochem.*, 188:349-355 (1990).
Khrapko et al., "An Oligonucleotide hybridization approach to DNA sequencing," *FEBS Lett.*, 256(1,2):118-122 (1989).
Khrapko et al., "A method for DNA sequencing by hybridization with oligonucleotide matrix," *DNA Seq. Map.*, 1:375-388 (1991).
Kievits et al., "Rapid subchromosomal localization of cosmids by nonradioactive in situ hybridization," *Cytogenetics and Cell Genetics*, 53:134-136 (1990).
Kimura et al., "An Immobilized Enzyme Membrane Fabrication Method using an Ink Jet Nozzle," *Biosensors*, 4:41-52 (1988).
Kitazawa et al., "In situ DNA-RNA hybridization using in vivo bromodeoxyuridine-labeled DNA probe," *Histochemistry*, 92:195-199 (1989).

Kleinfeld et al, "Controlled Outgrowth of Dissociated Neurons on Patterned Substrates" *J. Neuroscience*, 8:4098-4120 (1988).
Knutti, "Advanced Silicon Microstructures," presented at ASICT Conference Apr. 11, 1989, Toyohashih Japan.
Knutti, "Silicon Microsystems as a Industry," presented at microsystems 1990 (Sep. 10-13 1990 Berlin, Germany).
Knutti, "Emerging Silicon Microstructures," undated.
Kohara et al., "The Physical Map of the Whole *E. coli* Chromosome: Application of a New Strategy for Rapid Analysis and Sorting of a Large Genomic Library," *Cell*, 50:495-508 (1987).
Kuriyama, "An ISFET Biosensor," from *Applied Biosensors*, D. Wise, eds., Butterworths, pp. 93-114 (1989).
Kyser et al., "Design of an Impulse Ink Jet," *J. Appl. Photographic Eng.*, 7(3):73-79 (1981).
Lainer, et al, "Human Lymphocyte Subpopulations Identified by Using Three-Color Immunofluorescence and Flow Cytometry Analysis", *Journal of Immunology*, 132(1):151-156 (1984).
Larin et al, "Yeast artificial chromosome libraries containing large inserts from mouse and human DNA," *PNAS*, 88:4123-4127 (1991).
Laskey et al, "Messenger RNA prevalence in sea urchin embryos measured with cloned cDNAs," *PNAS*, 77(9):5317-5321 (1986).
Lehrach et al., "Hybridization Fingerprinting in Genome Mapping and Sequencing," *Genome Analysis vol. 1: Genetic and Physical Mapping*, Cold Spring Harbor Laboratory Press, pp. 39-81 (1990).
Lennon et al., "Hybridization Analyses of Arrayed cDNA Libraries," *Trends Genet.*, 7(10)314-317 (1991).
Lewin, Benjamin, eds., *Genes*, third edition, John Wiley & Sons, cover page, preface and table of contents, (1987).
Lichter et al., "Fluorescence in situ hybridization with Alu and Li polymerase chain reaction probes for. rapid characterization of human chromosomes in hybrid cell lines," *PNAS*, 87:6634-6638 (1990).
Lichter et al., "High-Resolution Mapping of Human Chromosome 11 by in Situ Hybridization with Cosmid Clones," *Science*, 247:64-69 (1990).
Lichter et al., "Is non-isotopic in situ hybridization finally coming of age?," *Nature*, 345:93-94 (1990).
Lichter et al., "Rapid detection of human chromosome 21 aberrations by in situ hybridization," *PNAS*, 85:9664-9668 (1988).
Little, P., "Clone maps made simple," *Nature*, 346:611-612 (1990).
Loken et al., "Three-Color Immunofluorescence Analysis of Leu Antigens on Human Peripheral Blood Using Two Lasers on a Flourescence-Activated Cell Sorter," *Cymoetry*, 5:151-158 (1984).
Longmire et al., "Automated Construction of High Density Gridded Arrays of Chromosome-Specific Cosmid Libraries," *LRA*, 3:195-198 (1991).
Love et al., "Screening of λ Library for Differentially Expressed Genes Using in Vitro Transcripts," *Anal. Biochem.*, 150:429-441 (1985).
Lu et al., "Differential screening of murine ascites cDNA libraries by means of in vitro transcripts of cell-cycle-phase-specific cDNA and digital image processing," *Gene*, 86:185-192 (1990).
Lysov et al., "A new method for determining the DNA nucleotide sequence by hybridization with oligonucleotides " *Doklady Biochem.*, 303(1-6):436-438 (1989).
Lysov et al., "DNA Sequencing by Oligonucleotide Hybridization," First International Conference on Electrophoresis, Supercomputing and the Human Genome, Apr. 10-13, 1990 pp. 157-163.
Masiakowski, et al., "Cloning of cDNA sequences of hormone-regulated genes from the MCF-7 human breast cancer cell line," *Nuc. Acids Res.*, 10(24):7895-7903 (1982).
Matthes et al., "Simultaneous rapid chemical synthesis of over one hundred oligonucleotides on a microscale," *EMBO J.*, 3(4):801-805 (1984).
McCray et al., "Properties and Uses of Photoreactive Caged Compounds," *Annu. Rev. Biophys. Biophys. Chem.*, 18:239-270 (1989).
Meinkoth et al., "Review: Hybridization of Nucleic Acids Immobilized on solid Supports," *Analytical Biochem.*, 138:267-284 (1984).
Merrifield, "Solid Phase Peptide Synthesis. I. The Synthesis of a Tetrapeptide," *J. Am. Chem. Soc.* 85:2149-2154 (1963).
Michels et al., "Molecular approaches to genome analysis: a strategy for the construction of ordered overlapping clone libraries," *CABIOS*, 3(3):203-210 (1987).

Miyada et al., "Oligonucleotide Hybridization Techniques," Meth. Enzymology, 154:94-107 (1987).

Monaco et al., "Human Genome Linking with Cosmids and Yeast Artificial Chromosomes", abstract from CSHS, p. 50, (1989).

Morrison et al., "Solution-Phase Detection of Polynucleotides Using Interacting Fluorescent Labels and Competitive Hybridization," *Analytical Biochemistry*, 183:231-244 (1989).

Nakamori et al., "A Simple and Useful Method for Simultaneous Screening of Elevated Levels of Expression of a Variety of Oncogenes in Malignant Cells," *Jpn. J. Cancer Res.*, 79:1311-1317 (1988).

Nederlof et al., "Multiple Fluorescence In Situ Hybridization," *Cytometry*, 11:126-131 (1990).

Newman et al., "Ink jet printing for the fabrication of amperometric glucose biosensors," *Anal. Chimica Acta*, 262:13-17 (1992).

Nizetic et al., "An improved bacterial colony lysis procedure enables direct DNA hybridisation using short (10, 11 bases) oligonucleotides to cosmids," *Nuc. Acids Res.*, 19(1):182 (1990).

Nizetic et al., "Construction, arraying, and high-density screening of large insert libraries of human chromosomes X and 21: their potential use as reference libraries," *PNAS*, 88:3233-3237 (1991).

Pillai, "Photoremovable Protecting Groups in Organic Synthesis", *Synthesis*, 1:1-16 (1980).

Poustka et al., "Molecular Approaches to Mammalian Genetics," Cold Spring Harbor Symposia on Quantitive Biology, 51:131-139 (1986).

Raoult et al., "The Line Blot: an immunoassay for monoclonal and other antibodies " *J. Immunological Meth.*, 125:57-65 (1989).

Ross et al., "High-Density Gridded YAC Filters: their Potential as Genome Mapping Tools," from *Techniques for the Analysis of Complex Genomes*, chapter 8, pp. 137-153 (1992).

Saiki et al., "Genetic analysis of amplified DNA with immobilized sequence-specific oligonucleotide probes," *PNAS*, 86:6230-6234 (1989).

Sambrook, Molecular Cloning—A Laboratory Manual, publ. in 1989.

Scharf et al., "HLA class II allelic variation and susceptibility to pemphigus vulgaris," *PNAS*, 85:3504-3508 (1988).

Seed, B., "Diazotizable arylamine cellulose papers for the coupling and hybridization of nucleic acids," *Nuc. Acids Res.*, 10(5):1799-1810 (1982).

Sim et al., "Use of a cDNA Library for Studies on Evolution and Developmental Expression of the Chorion Multigene Families," *Cell*, 18:1303-1316 (1979).

Southern et al., "Oligonucleotide hybridisations on glass supports: a novel linker for oligonucleotide synthesis and hybridization properties of oligonucleotides synthesized in situ," *Nuc. Acids Res.*, 20(7):1679-1684 (1992).

Southern et al., "Analyzing and Comparing Nucleic Acid Sequences by Hybridization to Arrays of Oligonucleotides: Evaluation Using Experimental Models," *Genomics*, 13:1008-1017 (1992).

Strezoska et al., "DNA Sequencing by hybridization: 100 bases read by a non-gel-based method," *PNAS*, 88:10089-10093 (1991).

Stryer, L, from *Biochemistry*, Fourth Edition, Chapter 2, pp. 20-23; W.H. Freeman & Co. (1995).

Stryer, L, "DNA Probes and Genes Can be Synthesized by Automated Solid-Phase Methods," from *Biochemistry*, Third Edition, pp. 123-124, published by W.H. Freeman & Co.; (1988).

Sze, "Lithography," chapter 7 from *VLSI Technology*, McGraw-Hill Book company, pp. 267-301 (1983).

Takada et al., "Effect of Ink Channel dimensions and Fluid Viscosity in Drop-on-Demand Ink-Jet Printing," *Fujitsu Sci. Tech. J.*, 22(2):132-138 (1986).

Teng et al., "A Microprocessor-Controlled Ink Jet Printing System for Electronic Circuits," *IEEE Trans. Indus. Elec.*, 35(3):407-412 (1988).

Teng et al., "Mathematical models of ink jet printing in thick-film hybrid microelectronics," *Appl. Math. Modelling*, 12:182-188 (1988).

Teng et al., "Ink Jet Printing in Thick Film Hybrid Microelectronics," Ph.D. thesis 35372, Purdue University, Dec. 19, 1986.

Titus et al., "Texas Red, A Hydrophilic, Red-Emitting Fluorophore for use with Fluorescein in Dual Parameter Flow Microfluorometric and Fluorescence Microscopic Studies " *Journal of Immunological Methods*, 50:193-204. (1982).

Tkachuk et al., "Detection of bcr-abl Fusion in Chronic Myelogenous Leukemia by in situ Hybridization," *Science*, 250:559-562 (1990).

Tonucci et al., "Nanochannel Array Glass," *Science*, 258:783-785 (1992).

Tsusumi et al., "Expression L-and M-'Type Pyruvate Kinase in Human Tissues " *Genomics*, 2:86-89 (1988).

Turchinskii et al., "Multiple Hybridization in Genome Analysis. The Reaction of Diamines and Bisulfate with Cytosine for Introduction of Nonradioactive Labels into DNA," from *Molekulyarnaya Biologiya* (English Translation), 22:1229-1235 (1988).

Uber et al., "Application of robotics and image processing to automated colony picking and arraying," *BioTechniques*, 11(5):642-647 (1991).

Urdea et al., "A comparison of non-radioisotopic hybridization assay methods using fluorescent, chemiluminescent and enzyme labeled synthetic oligodeoxyribonucleotide probes," *Nuc. Acids Res.*, 16:4937-4956 (1988).

Urdea et al., "A-Novel Method for the Rapid Detection of Specific Nucleotide Sequences in Crude Biological Samples Without Blotting or Radioactivity; Application to the Analysis of Hepatitis B Virus in Human Serum," *Gene*, 61,253-264 (1987).

Wallace et al., "The Application of Ink-Jet Technology to Neuroscience Research and Biomedical Research," from *Proceedsing Bioprocess Eng. Symp.* (Diller et al, eds.), pp. 153-158 (1989).

Wallace, D.B., "Automated Electronic Circuit Manufacturing Using Ink-Jet Technology," *J. Electronic Packaging*, 111:108-111 (1989).

Wallace et al., "Hybridization of synthetic oligodeoxyribonucleotides to *x 174 DNA: the effect of single base pair mismatch", *Nuc. Acids Res.*, 6(11):3543-3557 (1979).

Widacki et al., "Biochemical Differences in Qa-2 Antigens Expressed by Qa-2+,6+ and Qa-2+,6- Strains. Evidence for Differential Expression of the Q7 and Q9 Genes," *Molecular Immunology*, 27(6):559-570 (1990).

Wu et al., "Laboratory Methods, Direct Analysis of Single Nucleotide Variation in Human DNA and RNA Using in Situ Dot Hybridization," *DNA*, 8(2):135-142 (1989).

Wu et al., "Synthesis and Properties of Adnosine-5'-triphosphoro-y-I-(5-sulfonic acid) naphthyl Ethylamidate: A Fluorescent Nucleotide Substrate for DNA-Dependent RNA Polymerase from *Escherichia coli*" *Arch. Biochem. Biophys.*, 246:564-71 (1989).

Yarbrough, et al., "Synthesis and Properties of Fluorescent Nucleotide Substrates for DNA-dependent RNA Polymerases," *J. Biol. Chem.*, 254:12069-73 (1979).

Young , "Simultaneous Use of Digoxigenin-and Radiolabeled Oligodeoxyribonucleotide Probes for Hybridization Histochemistry," *Neuropeptides*, 13:271-275 (1989).

CA 116(11):106500s; Stjernloef (1991).

"Preparation of fluorescence-labeled DNA and its use as a probe in molecular hybridization," Bioorg Khim, 12:1508-13.

Declaration of Dr. Thomas Gingeras dated Jan. 14, 1999 in the Matter of European Patent No. EP 0 373 203 of Isis Limited and Opposition thereto by Affymetrix.

Expert Report of David Bowen Wallace dated Jan. 18, 2001.

First Witness Statement of Alan Blanchard dated Jan. 19, 2001 in European Opposition by Protogene Laboratories, Inc. to EP 0 619 321.

Expert Report of Ronald Gamble dated Jan. 21, 2001.

Expert Report of Anthony Cass (Non-Confidential Version) dated Jan. 22, 2001 in the High Court of Justice, Chancery Division, Patents Court Claim No. HC-1999-02517, the Matter of European Patent 0 619 321B and in the Matter of a Claim for Revocation by Oxford Gene Technology Ltd.

Supplemental Expert Report of Ronald Gamble dated Mar. 8, 2001 in the High Court of Justice, Chancery Division, Patents Court Claim No. HC-1999-02517, the Matter of European Patent 0 619 321B and in the Matter of a Claim for Revocation by Oxford Gene Technology Ltd.

Supplemental Expert Report of Anthony Cass dated Mar. 15, 2001 in the High Court of Justice, Chancery Division, Patents Court Claim No. HC-1999-02517, the Matter of European Patent 0 619 321B and in the Matter of a Claim for Revocation by Oxford Gene Technology Ltd.

Declaration of Grant Morgan dated Sep. 6, 2002 in the Matter or European Patent No. EP 1086742.

Declaration of Anthony Cass dated Jul. 17, 2003 in the Matter of European Patent Application No. EP 0 619 321 in the Name of Affymetrix, Inc., and in the Matter of Oppositions thereto.

Declaration of Anthony Cass in the Matter of European Patent Application No. EP 99 202455.4 in the Name of Affymetrix, Inc. (2003).

Notice of Opposition to EP 0972564 by Applera Corporation dated Feb. 26, 2004.

Declaration of Professor John David Sutherland dated Jan. 4, 2005 in the Matter or European Patent No. 0972564.

Declaration of Professor Anthony Cass dated Jan. 5, 2005 In the Matter or European Patent No. 0972564.

Response of the Patentee Affymetrix Inc. to the Opposition dated Jan. 12, 2005.

Response of the Patentee Affymetrix to Opposition Against EP 1086742 by Degussa AG dated Aug. 8, 2005.

Opposition Division Communication of Facts and Submissions dated Feb. 3, 2006 in the Matter of European Patent No. 1086742.

Declaration of Professor John David Sutherland dated Jun. 7, 2006 in the Matter or European Patent No. 0972564.

Interlocutory Decision in Opposition Proceedings in European Patent No. EP 1086742 dated Jul. 26, 2006.

Decision Revoking the European Patent dated Jul. 31, 2006 in the Matter or European Patent No. EP 0972564.

Excerpts from Grant Proposal by Dr. Ron Davis, Professor, Department of Genetics, Stanford University.

* cited by examiner

COMBINATORIAL STRATEGIES FOR POLYMER SYNTHESIS

This application is a continuation of U.S. patent application Ser. No. 09/579,982, filed on May 26, 2000; which in turn is a continuation of U.S. patent application Ser. No. 09/498,554, filed on Feb. 4, 2000; which in turn is a continuation of U.S. patent application Ser. No. 09/129,463, filed on Aug. 4, 1998, now U.S. Pat. No. 6,040,193; which in turn is a continuation of U.S. patent application Ser. No. 08/426,202, filed Apr. 21, 1995, now U.S. Pat. No. 6,136,269; which in turn is a continuation of U.S. patent application Ser. No. 07/980,523, filed Nov. 20, 1992, now U.S. Pat. No. 5,677,195; which in turn is a continuation-in-part of U.S. patent application Ser. No. 07/874,849, filed Apr. 24, 1992, now U.S. Pat. No. 5,412,087, and of U.S. patent application Ser. No. 07/796,243, filed Nov. 22, 1991, now U.S. Pat. No. 5,384,261.

BACKGROUND OF THE INVENTION

The present invention relates to the field of polymer synthesis and screening. More specifically, in one embodiment the invention provides an improved method and system for synthesizing arrays of diverse polymer sequences. According to a specific aspect of the invention, a method of synthesizing diverse polymer sequences such as peptides or oligonucleotides is provided. The diverse polymer sequences may be used, for example, in screening studies for determination of binding affinity.

Methods of synthesizing desired polymer sequences such as peptide sequences are well known to those of skill in the art. Methods of synthesizing oligonucleotides are found in, for example, *Oligonucleotide Synthesis: A Practical Approach*, Gate, ed., IRL Press, oxford (1984), incorporated herein by reference in its entirety for all purposes. The so-called "Merrifield" solid phase peptide sysnthesis has been in common use for several years and is described in Merrifield, J. Am. Chem. Soc. (1963) 85:2149-2154, incorporated herein by reference for all purposes. Solid-phase synthesis techniques have been provided for the synthesis of several peptide sequences on, for example, a number of "pins." See e.g., Geysen et al., *J. Immun. Meth.* (1987) 102:259-274, incorporated herein by reference for all purposes. Other solid-phase techniques involve, for example, synthesis of various peptide sequences on different cellulose disks supported in a column. See Frank and Doring, *Tetrahedron* (1988) 44:6031-6040, incorporated herein by reference for all purposes. Still other solid-phase techniques are described in U.S. Pat. No. 4,728,502 issued to Hamill and WO 90/00626 (Beattie, inventor).

Each of the above techniques produces only a relatively low density array of polymers. For example, the technique described in Geysen et al. is limited to producing 96 different polymers on pins spaced in the dimensions of a standard microtiter plate.

Improved methods of forming large arrays of peptides, oligonucleotides, and other polymer sequences in a short period of time have been devised. Of particular note, Pirrung et al., U.S. Pat. No. 5,143,854 (see also PCT Application No. WO 90/15070) and Fodor et al., PCT Publication No. WO 92/10092, all incorporated herein by reference, disclose methods of forming vast arrays of peptides and other polymer sequences using, for example, light-directed synthesis techniques. See also, Fodor et al., *Science* (1991) 251:767-777, also incorporated herein by reference for all purposes.

Some work has been done to automate synthesis of polymer arrays. For example, Southern, PCT Application No. WO 89/10977 describes the use of a conventional pen plotter to deposit three different monomers at twelve distinct locations on a substrate. These monomers were subsequently reacted to form three different polymers, each twelve monomers in length. The Southern Application also mentions the possibility of using an ink-jet printer to deposit monomers on a substrate. Further, in the above-referenced Fodor et al., PCT application, an elegant method is described for using a computer-controlled system to direct a VLSIPS™ procedure. Using this approach, one heterogenous array of polymers is converted, through simultaneous coupling at a number of reaction sites, into a different heterogenous array. This approach is referred to generally as a "combinatorial" synthesis.

The VLSIPS™ techniques have met with substantial success. However, in some cases it is desirable to have alternate/additional methods of forming polymer sequences which would not utilize, for example, light as an activator, or which would not utilize light exclusively.

SUMMARY OF THE INVENTION

Methods and devices for synthesizing high-density arrays of diverse polymer sequences such as diverse peptides and oligonucleotides are provided by virtue of the present invention. In addition, methods and devices for delivering (and, in some cases, immobilizing) available libraries of compounds on specific regions of a substrate are provided by this invention. In preferred embodiments, various monomers or other reactants are delivered to multiple reaction sites on a single substrate where they are reacted in parallel.

According to a preferred embodiment of the invention, a series of channels, grooves, or spots are formed on or adjacent a substrate. Reagents are selectively flowed through or deposited in the channels, grooves, or spots, forming an array having different compounds—and in some embodiments, classes of compounds—at selected locations on the substrate.

According to the first specific aspect of the invention, a block having a series of channels, such as grooves, on a surface thereof is utilized. The block is placed in contact with a derivatized glass or other substrate. In a first step, a pipettor or other delivery system is used to flow selected reagents to one or more of a series of apertures connected to the channels, or place reagents in the channels directly, filling the channels and "striping" the substrate with a first reagent, coupling a first group of monomers thereto. The first group of monomers need not be homogenous. For example, a monomer A may be placed in a first group of the channels, a monomer B in a second group of channels, and a monomer C in a third group of channels. The channels may in some embodiments thereafter be provided with additional reagents, providing coupling of additional monomers to the first group of monomers. The block is then translated or rotated, again placed on the substrate, and the process is repeated with a second reagent, coupling a second group of monomers to different regions of the substrate. The process is repeated until a diverse set of polymers of desired sequence and length is formed on the substrate. By virtue of the process, a number of polymers having diverse monomer sequences such as peptides or oligonucleotides are formed on the substrate at known locations.

According to the second aspect of the invention, a series of microchannels or microgrooves are formed on a substrate, along with an appropriate array of microvalves. The channels and valves are used to flow selected reagents over a derivatized surface. The microvalves are used to determine which of the channels are opened for any particular coupling step.

Accordingly, one embodiment of the invention provides a method of forming diverse polymer sequences on a single substrate, the substrate comprising a surface with a plurality of selected regions. The method includes the steps of forming a plurality of channels adjacent the surface, the channels at least partially having a wall thereof defined by a portion of the selected regions; and placing selected reagents in the channels to synthesize polymer sequences at the portion of the selected regions, the portion of the selected regions comprising polymers with a sequence of monomers different from polymers in at least one other of the selected regions. In alternative embodiments, the channels or flow paths themselves constitute the selected reaction regions. For example, the substrate may be a series of adjoining parallel channels, each having reaction sites therein.

According to a third aspect of the invention, a substrate is provided which has an array of discrete reaction regions separated from one another by inert regions. In one embodiment, a first monomer solution is spotted on a first set of reaction regions of a suitably derivatized substrate. Thereafter, a second monomer solution is spotted on a second set of regions, a third monomer solution is spotted on a third set and so on, until a number of the regions each have one species of monomer located therein. These monomers are reacted with the surface, and the substrate is subsequently washed and prepared for reaction with a new set of monomers. Dimers, trimers, and larger polymers of controlled length and monomer sequence are prepared by repeating the above steps with different groupings of the reaction regions and monomer solutions. In alternative embodiments, the polymers or other compounds of the array are delivered to the regions as complete species, and thus the above polymer synthesis steps are unnecessary.

In a preferred embodiment, a plurality of reaction regions on the substrate surface are surrounded by a constraining region such as a non-wetting region which hinders the transport of reactants between adjacent reaction regions. Thus, the reactants in one region cannot flow to other regions where they could contaminate the reaction. In certain preferred embodiments, the regions of the array are defined by selective irradiation of a substrate surface containing photolabile hydrophobic protecting groups. In areas where the surface is irradiated, the hydrophobic protecting groups are removed to define reaction regions. When an aqueous or other polar reactant solution is deposited in the reaction region, it will have a relatively large wetting angle with the substrate surface so that by adjusting the amount deposited, one can ensure no flow to adjacent regions.

A further understanding of the nature and advantages of the inventions herein may be realized by reference to the remaining portions of the specification and the attached drawings.

BRIEF DESCRIPTION OF THE DRAWINGS

FIG. 3 is a mapping of a resulting array of polymers.

DESCRIPTION OF THE PREFERRED EMBODIMENTS

CONTENTS

Figure 1:
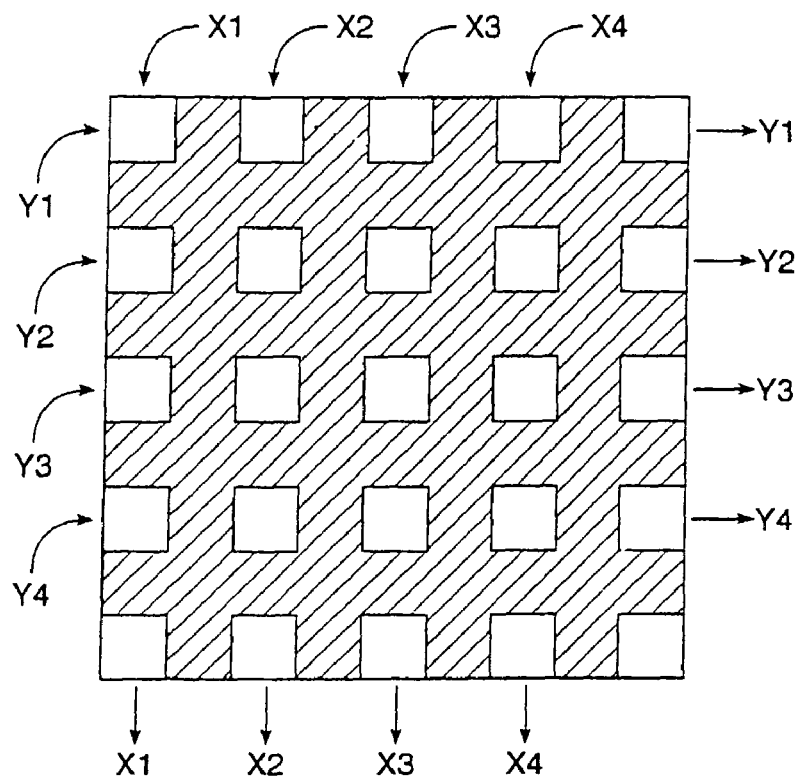
FIG. 1 is a generalized diagram illustrating the invention.

I. Glossary
II. General
III. Methods for Mechanical Delivery of Reagents
IV. Flow Channel Embodiments
V. Spotting Embodiments
VI. Alternative Embodiments
VII. Examples
   A. Leak Testing
   B. Formation of YGGFL
   C. 100 Micron Channel Block
   D. Channel Matrix Hybridization Assay
VIII. Conclusion I. Glossary The following terms are intended to have the following general meanings as they are used herein:
1. Ligand: A ligand is a molecule that is recognized by a receptor. Examples of ligands that can be investigated by this invention include, but are not restricted to, agonists and antagonists for cell membrane receptors, toxins and venoms, viral epitopes, hormones, opiates, steroids, peptides, enzyme substrates, cofactors, drugs, lectins, sugars, oligonucleotides, nucleic acids, oligosaccharides, and proteins.
2. Monomer: A monomer is a member of the set of small molecules which are or can be joined together to form a polymer or a compound composed of two or more members. The set of monomers includes but is not restricted to, for example, the set of common L-amino acids, the set of D-amino acids, the set of synthetic and/or natural amino acids, the set of nucleotides and the set of pentoses and hexoses. The particular ordering of monomers within a polymer is referred to herein as the "sequence" of the polymer. As used herein, monomers refers to any member of a basis set for synthesis of a polymer. For example, dimers of the 20 naturally occurring L-amino acids form a basis set of 400 monomers for synthesis of polypeptides. Different basis sets of monomers may be used at successive steps in the synthesis of a polymer. Furthermore, each of the sets may include protected members which are modified after synthesis. The invention is described herein primarily with regard to the preparation of molecules containing sequences of monomers such as amino acids, but could readily be applied in the preparation of other polymers. Such polymers include, for example, both linear and cyclic polymers of nucleic acids, polysaccharides, phospholipids, and peptides having either $\alpha$-, $\beta$-, or $\omega$-amino acids, heteropolymers in which a known drug is covalently bound to any of the above, polynucleotides, polyurethanes, polyesters, polycarbonates, polyureas, polyamides, polyethyleneimines, polyarylene sulfides, polysiloxanes, polyimides, polyacetates, or other polymers which will be apparent upon review of this disclosure. Such polymers are "diverse" when polymers having different monomer sequences are formed at different predefined regions of a substrate. Methods of cyclization and polymer reversal of polymers are disclosed in copending application Ser. No. 796,727, filed Nov. 22, 1991, entitled "POLYMER REVERSAL ON SOLID SURFACES," incorporated herein by reference for all purposes.

3. Peptide: A peptide is a polymer in which the monomers are alpha amino acids and are joined together through amide bonds, alternatively referred to as a polypeptide. Amino acids may be the L-optical isomer or the D-optical isomer. Peptides are two or more amino acid monomers long and are often more than 20 amino acid monomers long. Standard abbreviations for amino acids are used (e.g., P for proline). These abbreviations are included in Stryer, *Biochemistry*, Third Ed., 1988, which is incorporated herein by reference for all purposes.

4. Receptor: A receptor is a molecule that has an affinity for a ligand. Receptors may be naturally-occurring or manmade molecules. They can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants, viruses, cells, drugs, polynucleotides, nucleic acids, peptides, cofactors, lectins, sugars, polysaccharides, cellular membranes, and organelles. Receptors are sometimes referred to in the art as anti-ligands. As the term receptors is used herein, no difference in meaning is intended. A "Ligand Receptor Pair" is formed when two molecules have combined through molecular recognition to form a complex.

Specific examples of receptors which can be investigated by this invention include but are not restricted to:

a) Microorganism receptors: Determination of ligands that bind to microorganism receptors such as specific transport proteins or enzymes essential to survival of microorganisms would be a useful tool for discovering new classes of antibiotics. Of particular value would be antibiotics against opportunistic fungi, protozoa, and bacteria resistant to antibiotics in current use.

b) Enzymes: For instance, a receptor can comprise a binding site of an enzyme such as an enzyme responsible for cleaving a neurotransmitter; determination of ligands for this type of receptor to modulate the action of an enzyme that cleaves a neurotransmitter is useful in developing drugs that can be used in the treatment of disorders of neurotransmission.

c) Antibodies: For instance, the invention may be useful in investigating a receptor that comprises a ligand-binding site on an antibody molecule which combines with an epitope of an antigen of interest; determining a sequence that mimics an antigenic epitope may lead to the development of vaccines in which the immunogen is based on one or more of such sequences or lead to the development of related diagnostic agents or compounds useful in therapeutic treatments such as for autoimmune diseases (e.g., by blocking the binding of the "self" antibodies).

d) Nucleic Acids: Sequences of nucleic acids may be synthesized to establish DNA or RNA binding sequences that act as receptors for synthesized sequence.

e) Catalytic Polypeptides: Polymers, preferably antibodies, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant. Catalytic polypeptides and others are described in, for example, PCT Publication No. WO 90/05746, WO 90/05749, and WO 90/05785, which are incorporated herein by reference for all purposes.

f) Hormone receptors: Determination of the ligands which bind with high affinity to a receptor such as the receptors for insulin and growth hormone is useful in the development of, for example, an oral replacement of the daily injections which diabetics must take to relieve the symptoms of diabetes or a replacement for growth hormone. Other examples of hormone receptors include the vasoconstrictive hormone receptors; determination of ligands for these receptors may lead to the development of drugs to control blood pressure.

g) Opiate receptors: Determination of ligands which bind to the opiate receptors in the brain is useful in the development of less-addictive replacements for morphine and related drugs.

5. Substrate: A material having a rigid or semi-rigid surface. In many embodiments, at least one surface of the substrate will be substantially flat, although in some embodiments it may be desirable to physically separate synthesis regions for different polymers with, for example, wells, raised regions, etched trenches, or the like. In some embodiments, the substrate itself contains wells, trenches, flow through regions, etc. which form all or part of the synthesis regions. According to other embodiments, small beads may be provided on the surface, and compounds synthesized thereon may be released upon completion of the synthesis.

6. Channel Block: A material having a plurality of grooves or recessed regions on a surface thereof. The grooves or recessed regions may take on a variety of geometric configurations, including but not limited to stripes, circles, serpentine paths, or the like. Channel blocks may be prepared in a variety of manners, including etching silicon blocks, molding or pressing polymers, etc.

7. Protecting Group: A material which is bound to a monomer unit and which may be selectively removed therefrom to expose an active site such as, in the specific example of an amino acid, an amine group. Specific examples of photolabile protecting groups are discussed in Fodor et al., PCT Publication No. WO 92/10092 (previously incorporated by reference) and U.S. Ser. No. 07/971,181 filed Nov. 2, 1992 incorporated herein by reference for all purposes.

8. Predefined Region: A predefined region is a localized area on a substrate which is, was, or is intended to be used for formation of a selected polymer and is otherwise referred to herein in the alternative as "reaction" region, a "selected" region, or simply a "region." The predefined region may have any convenient shape, e.g., circular, rectangular, elliptical, wedge-shaped, etc. In some embodiments, a predefined region and, therefore, the area upon which each distinct polymer sequence is synthesized is smaller than about 1 cm$^2$, more preferably less than 1 mm$^2$, and still more preferably less than 0.5 mm$^2$. In most preferred embodiments the regions have an area less than about 10,000 μm$^2$ or, more preferably, less than 100 μm$^2$. Within these regions, the polymer synthesized therein is preferably synthesized in a substantially pure form.

9. Substantially Pure: A polymer is considered to be "substantially pure" within a predefined region of a substrate when it exhibits characteristics that distinguish it from other predefined regions. Typically, purity will be measured in terms of biological activity or function as a result of uniform sequence. Such characteristics will typically be measured by way of binding with a selected ligand or receptor. Preferably the region is sufficiently pure such that the predominant species in the predefined region is the desired sequence. According to preferred aspects of the invention, the polymer is at least 5% pure, more preferably more than 10% to 20% pure, more preferably more than 80% to 90% pure, and most preferably more than 95% pure, where purity for this purpose refers to the ratio of the number of ligand molecules formed in a predefined region having a desired sequence to the total number of molecules formed in the predefined region.

II. General

The invention can be used in variety of applications. For example, the invention can be used as a synthesis tool (as for example in peptide syntheses), as a screening tool (as for example in screening compound libraries for drug activity), or as a monitoring/diagnostic tool (as for example in medical or environmental testing). In one specific embodiment, the invention is used for nucleic acid-based diagnostics.

As a synthesis tool, the present invention provides for the formation of arrays of large numbers of different polymer sequences. According to a preferred embodiment, the invention provides for the synthesis of an array of different peptides or oligonucleotides in selected regions of a substrate. Such substrates having the diverse sequences formed thereon may be used in, for example, screening studies to evaluate their interaction with receptors such as antibodies and nucleic acids. For example, in preferred embodiments the invention provides for screening of peptides to determine which if any of a diverse set of peptides has a strong binding affinity with a receptor and, in most preferred embodiments, to determine the relative binding affinity of various peptides with a receptor of interest.

Such diverse polymer sequences are preferably synthesized on a single substrate. By synthesizing the diverse polymer sequences on a single substrate, processing of the sequences to evaluate characteristics such as relative binding affinity is more easily conducted. By way of example, when an array of peptide sequences (or a library of other compounds) is to be evaluated to determine the peptides' relative binding affinity to a receptor, the entire substrate and, therefore, all or a group of the polymer sequences may be exposed to an appropriately labelled receptor and evaluated simultaneously.

In some embodiments, the present invention can be employed to localize and, in some cases, immobilize vast collections of synthetic chemical compounds or natural product extracts. In such methods, compounds are deposited on predefined regions of a substrate. The reaction of the immobilized compound (or compounds) with various test compositions such as the members of the chemical library or a biological extract are tested by dispensing small aliquots of each member of the library or extract to a different region. Competitive assays or other well-known techniques can be used to identify a desired activity. As an example, a large collection of human receptors is deposited on a substrate, one in each region to form an array. A plant/animal extract is then screened for binding to various receptors of the array.

The present invention has certain features in common with the "light directed" methods described in U.S. Pat. No. 5,143,854, previously incorporated by reference. The light directed methods discussed in the '854 patent involve activating predefined regions of the substrate and then contacting the substrate with a preselected monomer solution. The predefined regions can be activated with a light source shown through a mask (much in the manner of photolithography techniques used in integrated circuit fabrication). Other regions of the substrate remain inactive because they are blocked by the mask from illumination. Thus, a light pattern defines which regions of the substrate react with a given monomer. By repeatedly activating different sets of predefined regions and contacting different monomer solutions with the substrate, a diverse array of polymers is produced on the substrate. Of course, other steps such as washing unreacted monomer solution from the substrate can be used as necessary.

In the present invention, a mechanical device or physical structure defines the regions which are available to react with a given monomer. In some embodiments, a wall or other physical barrier is used to block a given monomer solution from contacting any but a few selected regions of a substrate. In other embodiments, the amount of the monomer (or other) solution deposited and the composition of the substrate act to separate different monomer solutions on the substrate. This permits different monomers to be delivered and coupled to different regions simultaneously (or nearly simultaneously) and reduces the number of separate washing and other reaction steps necessary to form an array of polymers. Further, the reaction conditions at different activated regions can be controlled independently. Thus, the reactant concentrations and other parameters can be varied independently from reaction site to reaction site, to optimize the procedure.

In alternative preferred embodiments of the present invention, light or another activator is used in conjunction with the physical structures to define reaction regions. For example, a light source activates various regions of the substrate at one time and then a mechanical system directs monomer solutions to different activated regions, in parallel.

III. Methods for Mechanical Delivery of Reagents

In preferred embodiments of the present invention, reagents are delivered to the substrate by either (1) flowing within a channel defined on predefined regions or (2) "spotting" on predefined regions. However, other approaches, as well as combinations of spotting and flowing, may be employed. In each instance, certain activated regions of the substrate are mechanically separated from other regions when the monomer solutions are delivered to the various reaction sites.

A typical "flow channel" method of the present invention can generally be described as follows. Diverse polymer sequences are synthesized at selected regions of a substrate by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a linker) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

Various embodiments of the invention will provide for alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

The "spotting" embodiments of the present invention can be implemented in much the same manner as the flow channel embodiments. For example, a monomer A can be delivered to and coupled with a first group of reaction regions which have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire substrate surface can be sprayed or otherwise coated with a solution. In preferred embodiments, a dispenser moves from region to region, depositing only as much monomer as necessary at each stop. Typical dispensers include a micropipette to deliver the monomer solution to the substrate and a robotic system to control the position of the micropipette with respect to the substrate. In other embodiments, the dispenser includes a series of tubes, a manifold, an array of pipettes, or the like so that various reagents can be delivered to the reaction regions simultaneously.

IV. Flow Channel Embodiments

FIG. 1 illustrates an example of the invention. In this particular example, monomers and dimers of the monomer group A, B, C, and D are to be bound at selected regions of the substrate. The substrate may be biological, nonbiological, organic, inorganic, or a combination of any of these, existing as particles, strands, precipitates, gels, sheets, tubing, spheres, containers, capillaries, pads, slices, films, plates, slides, etc. The substrate may have any convenient shape, such as a disc, square, sphere, circle, etc. The substrate is preferably flat but may take on a variety of alternative surface configurations. For example, the substrate may contain raised or depressed regions on which the synthesis takes place.

The substrate and its surface form a support on which to carry out the reactions described herein. These monomers are bound using first flow channel paths $x_1$, $x_2$, $x_3$, and $x_4$ which are formed or placed on or adjacent the substrate in a first orientation, and second flow channel paths $y_1$, $y_2$, $y_3$, and $y_4$ which are formed or placed on or adjacent the substrate in a second orientation. The second flow channel paths intersect at least a part of the first flow channel paths. The flow channels are formed according to techniques which are described in greater detail elsewhere herein.

Initially the substrate is subjected to one or more preliminary treatments such as, for example, cleaning and the optional placement of "linker" molecules on the surface thereof. The substrate may also be provided with various active groups, common monomer sequences which will form a part of the polymers, or the like.

Thereafter, in a first coupling step, one or more of the flow channels are provided with the first monomer A, which binds through covalent bonds or otherwise to the substrate (directly or indirectly) where the flow channel contacts the substrate. In the particular example shown in FIG. 1, the flow channels $x_1$ and $x_2$ are utilized, binding the monomer A to the substrate along the entire length of the substrate adjacent to the $x_1$ and $x_2$ channels. Each coupling step may in some embodiments be composed of a variety of substeps. For example, each coupling step may include one or more substeps for washing, chemical activation, or the like.

Figure 2:
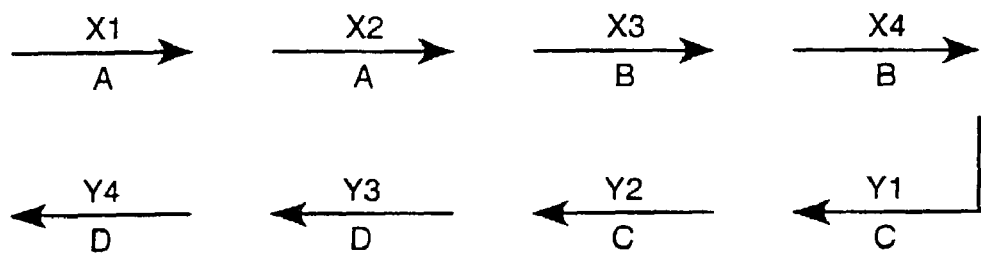
FIG. 2 is a flow chart illustrating the treatment steps performed in synthesizing an array of various polymers.

Thereafter or concurrently therewith, as shown in FIG. 2, a second monomer B is provided to selected flow channels and the monomer B binds to the substrate where the second flow channels provide contact therewith. In the particular example shown in FIG. 2, monomer B is bound along channels $x_3$ and $x_4$. When the monomers A and B flow through their respective flow channels simultaneously, only a single process step is required to perform two coupling steps simultaneously. As used herein, a "process step" refers to the injection of one or more channels with one or more reagents. A "coupling step" refers to the addition of a monomer in a polymer.

Processing thereafter continues in a similar manner with monomers C and D in the manner shown in the flow diagram of FIG. 2, with monomer C being bound in the flow channels $y_1$ and $y_2$, and D being bound in the flow channels $y_3$ and $y_4$.

Preferably, monomers C and D are directed through the flow channels $y_1$ to $y_4$ simultaneously whereby two coupling steps are performed with a single process step. Light regions in FIG. 1 indicate the intersections of the resulting flow paths.

Figure 3:
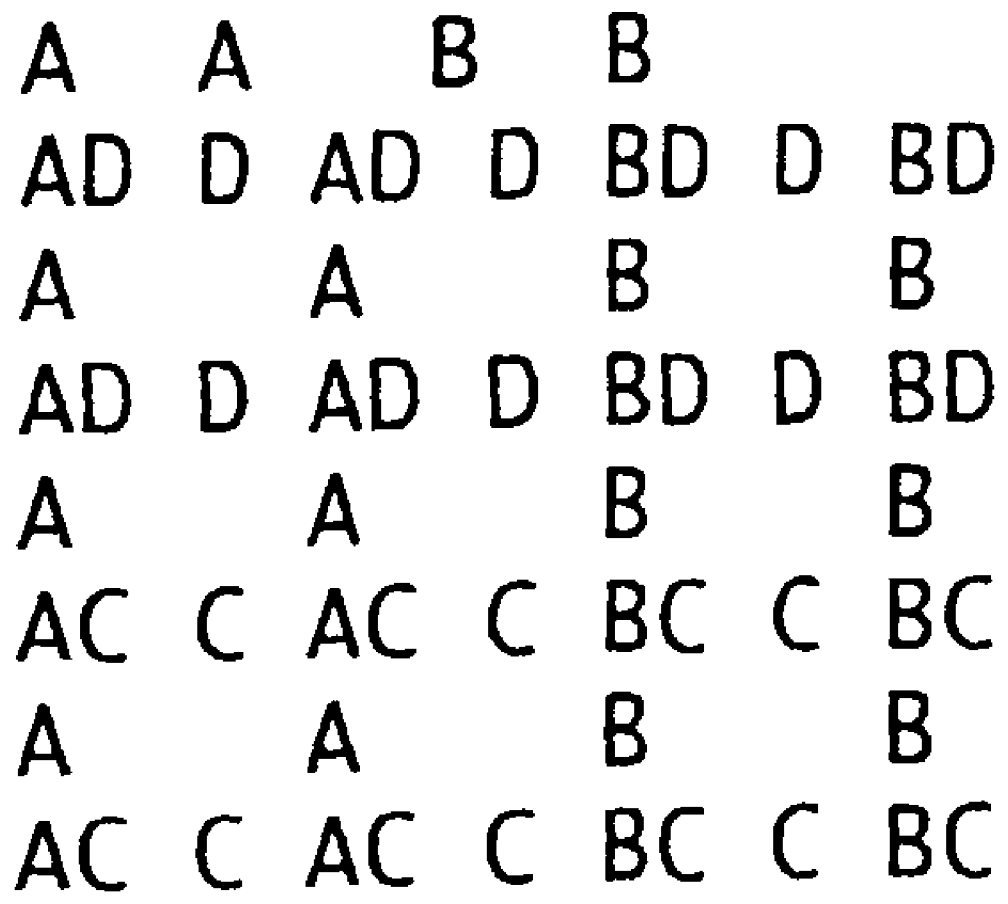

FIG. 3 illustrates the mapping of sequences formed using the above illustrated steps. As shown therein, the sequences A, B, C, D, AD, BD, AC, and BC have been formed using only two process steps. Accordingly, it is seen that the process provides for the synthesis of vast arrays of polymer sequences using only a relatively few process steps. By way of further example, it is necessary to use only two process steps to form all of the $4^2=16$ dimers of a four-monomer basis set. By way of further example, to form all $4^B$ octomers of a four-monomer basis set, it is necessary to provide only 256 flow channels oriented in the "x" direction, and 256 flow channels oriented in the "y" direction, with a total of eight coupling steps.

Figure 4A:
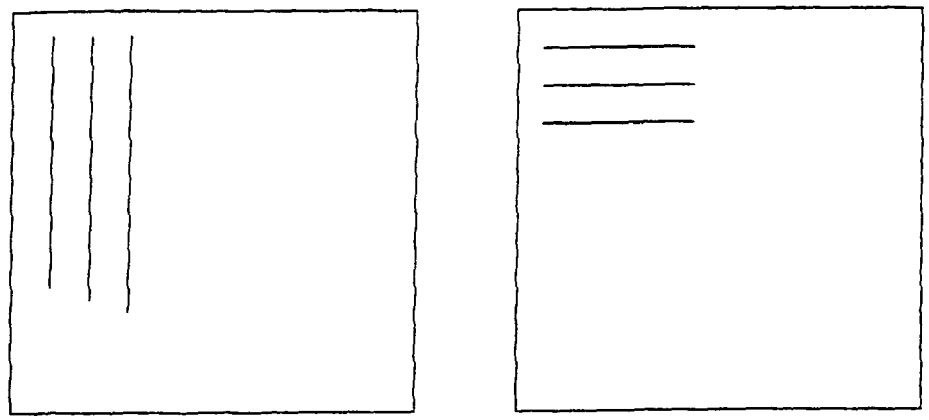
FIG. 4a to 4c illustrate the arrangement of three channel block templates in six process steps employed to synthesize 64 million hexapeptides from a 20 amino acid basis set.
Figure 4B:
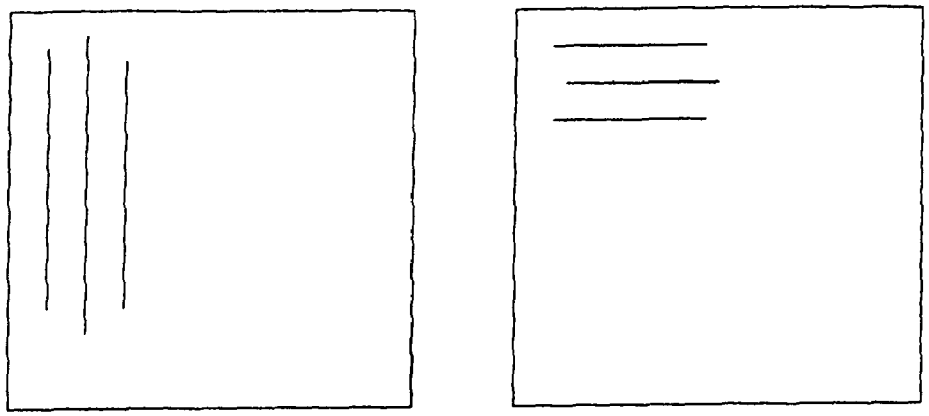
Figure 4C:
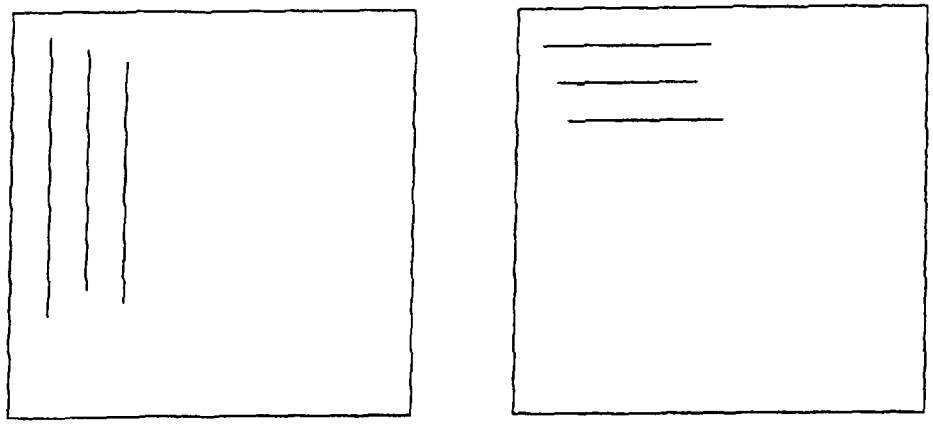

The power of the technique is further illustrated by synthesizing the complete array of six hexamer peptides from a 20 amino acid basis set. This array will include $20^6$ or 64,000,000 regions defining 64,000,000 different peptides and can be formed in only six process steps. Further, the method requires only three different templates, one having 20 parallel channels, a second having 400 channels each ½0th as wide as the first, and a third having 8000 channels each ½0th as wide as the second. Each template will be used in two process steps, each at an orientation at 90 degrees with respect to the other as illustrated in FIG. 4. With the first template, the substrate is activated and then solutions of each of the 20 amino acid basis set (or other 20 member basis set) are flowed over and reacted on a different predefined stripe in a first orientation. This is the first process step and includes 20 coupling or attachment steps, which can be performed simultaneously. Next, the entire substrate is again activated and the first template is placed in a second orientation, perpendicular to the first (FIG. 4a). The 20 amino acid solutions are then flowed along 20 new predefined stripes (each perpendicular to the original set of stripes). In each of these two process steps, the 20 predefined regions (the stripes along the flow channels) are first activated and then contacted with the individual monomers so that all 20 stripes are reacted before the next activation step is necessary. In other words, 20 coupling steps are conducted in parallel, greatly reducing the number of necessary activation steps.

The four remaining coupling steps employ the second and third templates. In the third and fourth process steps (FIG. 4b), 20 channels are devoted to each monomer, and in the fifth and sixth process steps (FIG. 4c), 400 channels are devoted to each monomer. As with the first two steps, the entire substrate undergoes reaction during a single process step. Thus, only six process steps (requiring a total of about 24 hours) are required to produce the entire library of 64,000,000 peptide hexamers. In a different embodiment, a single template having 8000 channels to control delivery (e.g. 400 channels for each of the 20 amino acids in the first round) can produce the full library of hexamers with only a single rotation step. Thus, the present invention offers extremely rapid methods of preparing diverse polymer arrays.

Figure 5A:
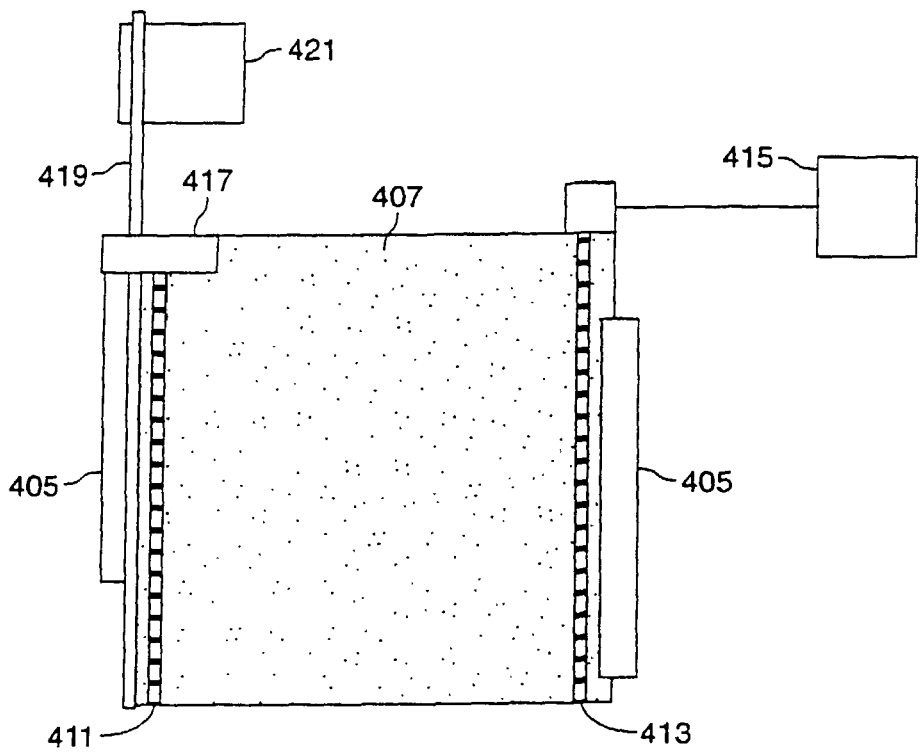
FIG. 5a is a top view and FIG. 5b is a cross-sectional view of a first embodiment of a device used to synthesize arrays of polymer sequences.
Figure 5B:
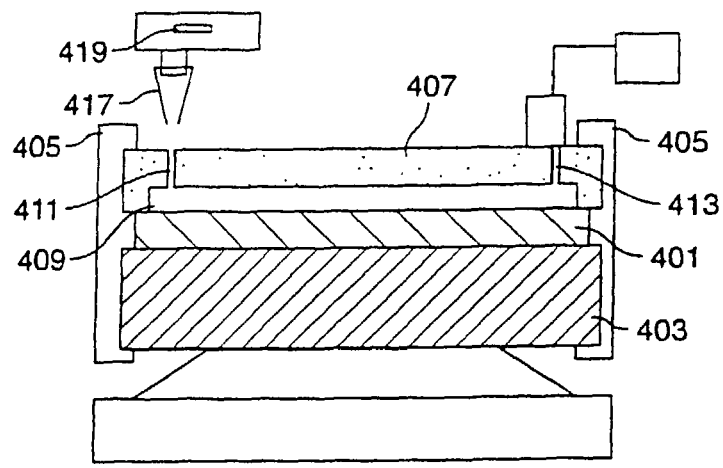

FIGS. 5a and 5b illustrate details of a first embodiment of a device used for performing the synthesis steps described above. In particular, FIG. 5a illustrates the device in top view, while FIG. 5b illustrates the device in cross-sectional side view. In the particular embodiment shown in FIG. 5, the device is used to synthesize polymer sequences on substrate 401. Substrate 401 is coupled to a rotating stage 403 and removably held by clamp 405 to channel block 407. Channel block 407 has etched therein a plurality of channels 409 in the form of stripes therein. Each channel is provided with a flow inlet 411 and an outlet 413. A vacuum source 415 is applied to one or more of the outlets 413, while a pipettor 417 is slidably mounted on arm 419 to deliver selected reagents from reservoir(s) 421 to selected flow inlets 411.

Figure 6:
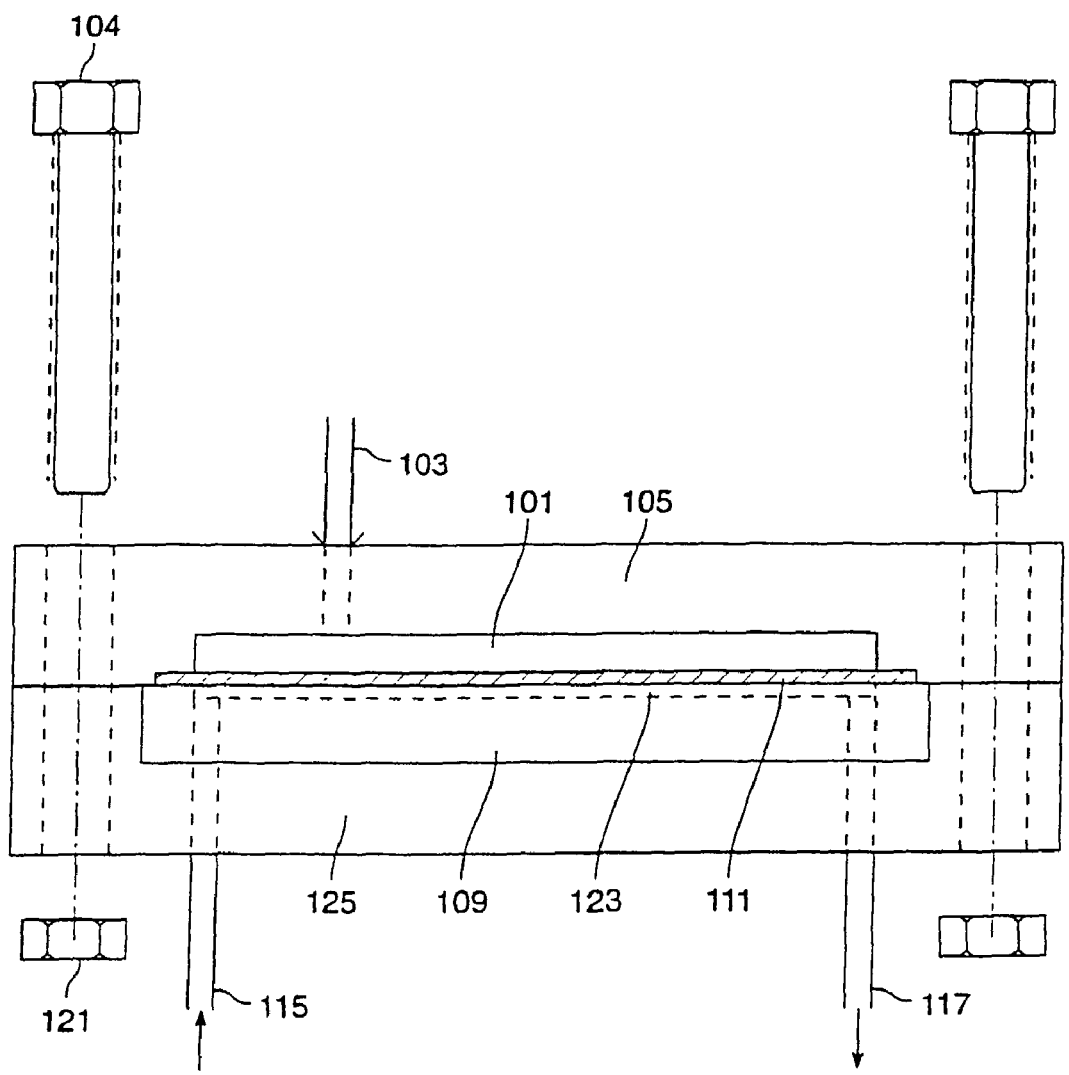
FIG. 6 is a cross-sectional view of an embodiment containing a pressure chamber for holding a substrate against a channel block.

The details of a second preferred embodiment are shown in FIGS. 6-11. FIG. 6 displays an apparatus for holding a substrate 111 in place against a channel block 109 by evenly distributing pressure over the substrate in a pressure chamber 101. Pressurized gas is admitted through gas pressure inlet 103 to provide clamping pressure to immobilize the substrate while fluids are flowed from fluid flow inlet 115, through channel 123, and out fluid outlet 117. The upper and lower portions of the pressure chamber housing 105 and 125 are held together by nuts 121 and bolts 104. Of course, other means such as clamps can be used to hold the pressure chamber housing portions together.

Figure 7A:
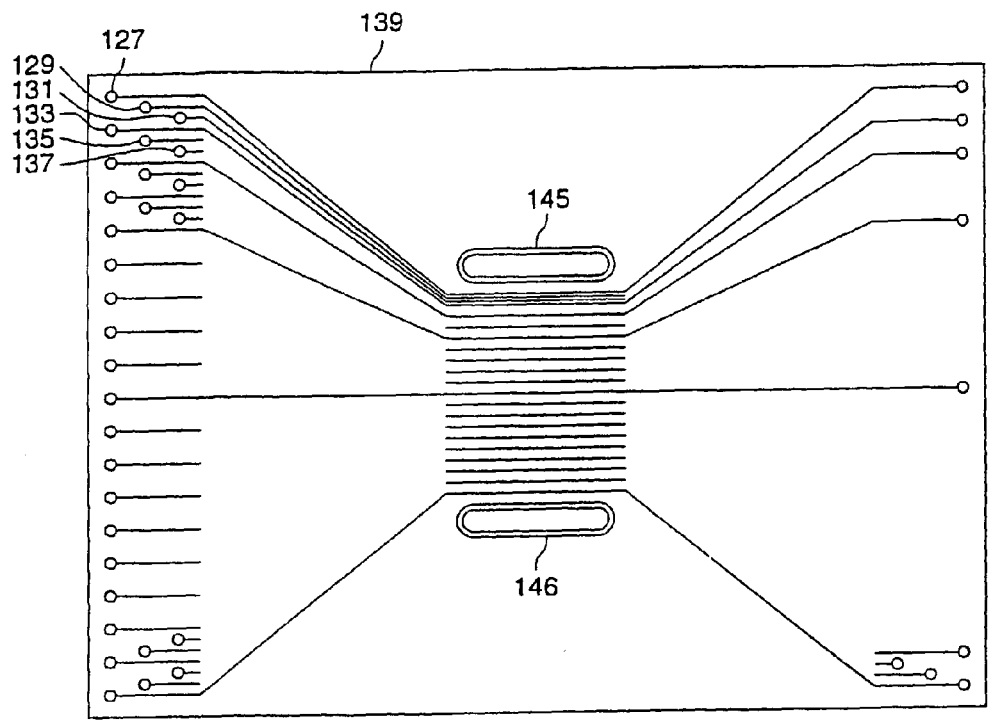
FIGS. 7a and 7b are top views of two of two different "fanned array" channel blocks.
Figure 7B:
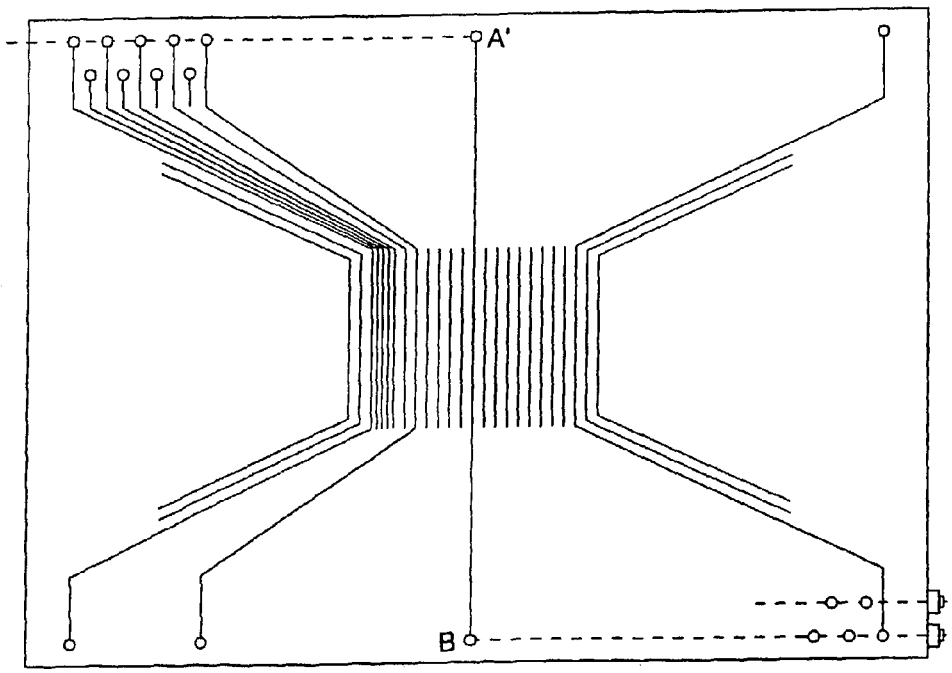

FIG. 7 illustrates preferred flow path configurations in channel blocks of the present invention. As shown in FIG. 7a, fluid delivery sites 127, 129, 131, 133, 135, and 137 are connected to channels leading to reaction region 141. A similar arrangement is shown for comparision in FIG. 7b where the orientation of the flow channels in the reaction regions is shifted by 90 degrees on a rectangular channel block. Vacuum ports 145 and 146 to an external vacuum line are provided so that substrate position is maintained during fluid flow.

The channels shown in FIGS. 7a and 7b form a "fanned channel array" on channel block 139 in a manner analogous to that of the lead pattern employed in integrated circuits. This provides significantly increased separation of fluid delivery points in comparison to the high density of channels in the reaction region. In a 2 inch by 3 inch substrate, at least about a 4:1 increase in spatial separation typically can be attained by the fanned arrangement. Thus, if the channels in the reaction regions are separated by 200 microns, the delivery ports can be separated by 0.8 mm.

The spatial separation can be further increased by staggering the delivery ports as shown for ports 127, 129, and 131. This can provide an additional channel separation of at least about 3:1. Thus, for the channels separated by 200 microns, a staggered fanned array provides 2.4 mm separation between the delivery ports. Thus, fluid can be delivered to a high-density array of of channels in the reaction region from standard 1.6 mm Teflon™ tubing. If additional spacing is necessary, the substrate size can be increased, while preserving the reaction region size.

Figure 8:
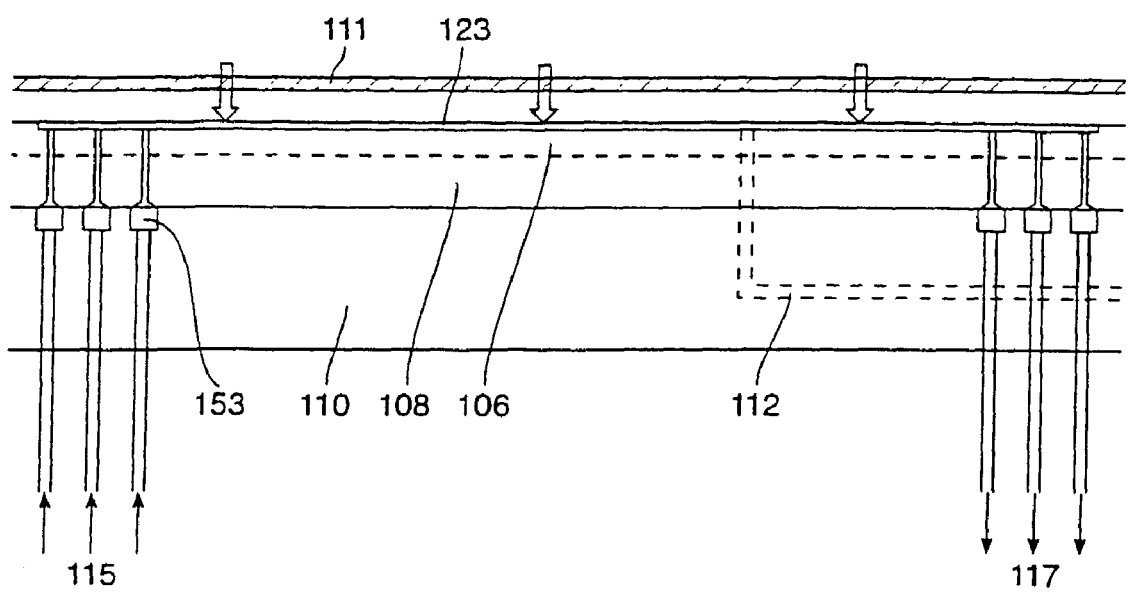
FIG. 8 is a cross-sectional view of a channel block and associated flow ports according to one embodiment of the invention.

As shown in FIG. 8, the fluid delivery ports are accessed from holes in the back surface of a stabilizing plate 108 on the channel block. The stabilizing plate, which is preferably made from fused pyrex, provides structural integrity to the channel block during clamping in the pressure chamber. It may also provide a means to access the channel block ports and reduce leakage between ports or channels. In preferred embodiments, the channels 123 of the channel block are formed on a wafer 106 which generally may be any machinable or cast material, and preferably may be etched silicon or a micromachined ceramic. In other embodiments, the channel block is pressure-formed or injection-molded from a suitable polymer material. The entire channel block arrangement is mounted on a rigid channel block sub-plate 110 including a vacuum line 112, ports for fluid delivery lines 115, ports for fluid outlet lines 117, and recessed regions for plug ends 151 and 153. With this arrangement, the substrate can be clamped against the top surface of the channel block (by vacuum or pressurized gas as shown in the embodiment of FIG. 6) while fluid enters and exits from below. Preferably, the subplate will be made from a rigid material such as stainless steel or anodized aluminum.

Figure 9:
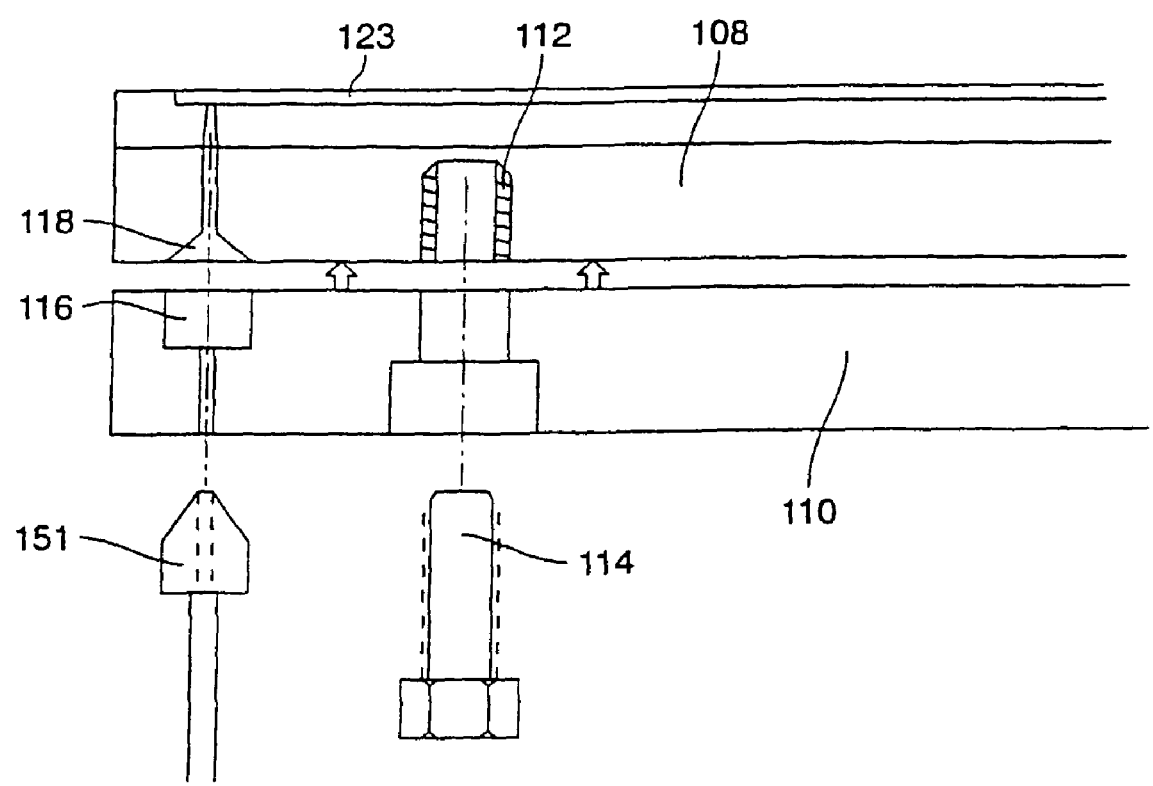
FIG. 9 is a detailed cross-sectioal view of the flow ports in a channel block.

Individual micro tubing connections can be made for each channel as shown in FIG. 9. Plug ends 151 are provided with a conical upper surface that mates with a conical recess 118 in pyrex stabilizing plate 108. Plug ends 151 also have a cylindrical lower surface that mates with cylindrical recess 116 in sub-plate 110. The subplate and stabilizing plate are held together by bolt 114 and threaded insert 112 or other suitable engagement means.

Figure 10:
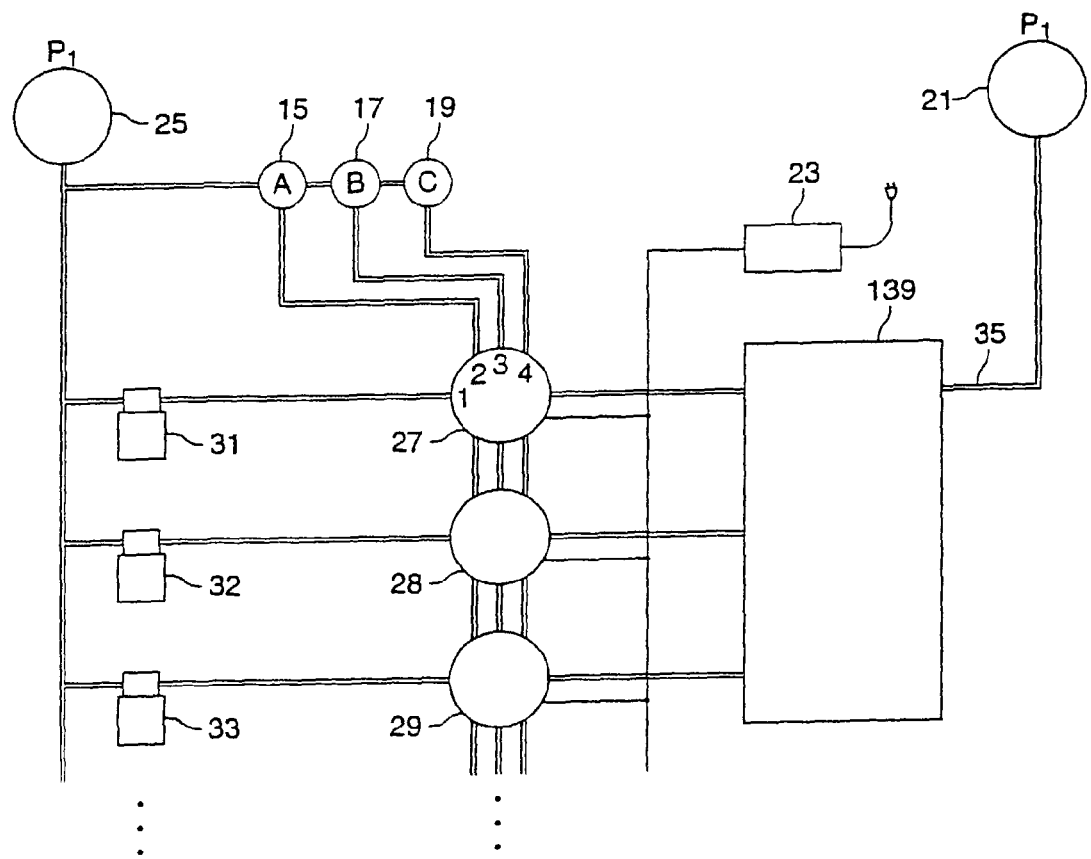
FIG. 10 is a diagram of a flow system used to deliver coupling compounds and reagents to a flow cell.

FIG. 10 shows a fluid flow diagram of a preferred system of the present invention. The pressure is controlled at point 25 (P1) and point 21 (P2) so that a pressure drop (P1-P2) is maintained across the system. Coupling compounds such as activated monomers are supplied from reservoirs 31, 32, and 33. Additional reagents are supplied from reservoirs 15, 17, and 19. Of course, the monomer and coupling reagent reservoirs shown in FIG. 10 are representative of a potentially much larger series of reservoirs. The reagents and coupling compounds are combined at nodes 27, 28, and 29 before being directed to channel block 139. Mixing of the appropriate reagents and coupling compounds is controlled by valves at the nodes which are in turn controlled by electronic control 23. Waste fluids that have been directed across the substrate are removed through line 35.

The system displayed in FIG. 10 allows control of all channels in parallel by regulating only a few variables. For example, a constant pressure gradient is maintained across all channels simultaneously by fixing P1 and P2. Thus, the flow rate in each channel is dependent upon the cross-sectional area of the flow channel and the rheological properties of the fluids. Because the channels have a uniform cross-section and because the coupling compounds are typically provided as dilute solutions of a single solvent, a uniform flow rate is created across all channels. With this system the coupling time in all channels can be varied simultaneously by simply adjusting the pressure gradient across the system. The valves of the system are preferably controlled by a single electronic output from control 23.

Figure 11A:
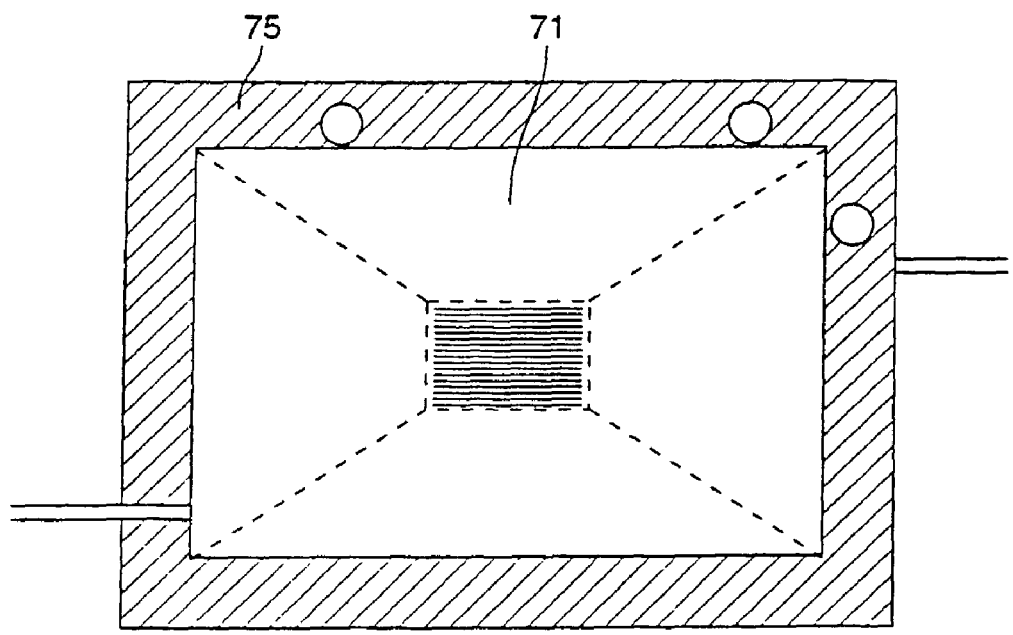
FIGS. 11a and 11b show an apparatus used to transfer a substrate from one channel block to another.
Figure 11B:
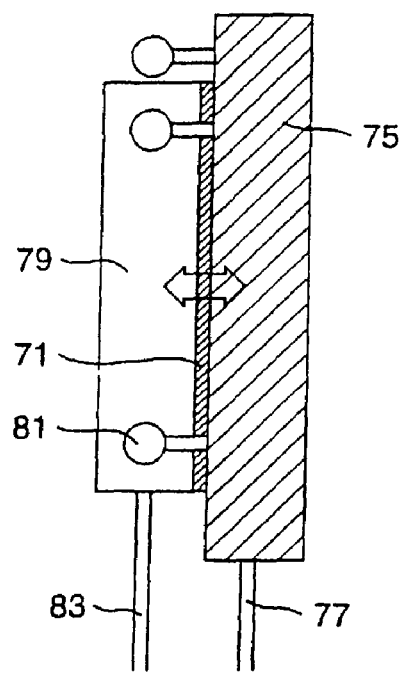

The fanned channel array design shown in FIG. 7 provides for two separate channel blocks to be used in successive process steps during a chemical synthesis. One block forms a horizontal array on the solid substrate, while the other block forms a vertical array. To create a matrix of intersecting rows and columns of chemical compounds, the solid substrate is transferred from one block to the other during successive process steps. While many experiments require only a single transfer from one block to the other during a series of process steps, the fanned channel array transfer block 75 illustrated in FIGS. 11a and 11b provides one device for maintaining accurate registration of the solid substrate 71 relative to the channel blocks 79 during repeated transfers. In some embodiments, a single channel block can be used for horizontal and vertical arrays by simply rotating it by 90 degrees as necessary.

The transfer block is positioned with respect to the channel block so that the dimensional characteristics of the solid substrate are not used in the alignment. The transfer block 75 is aligned to the channel block by kinematic mount 81 while vacuum is switched from vacuum line 83 on the channel block to vacuum line 77 on the transfer block (during normal operation, a vacuum holds the substrate against the channel block). The substrate and transfer block are then moved and repositioned relative to the second channel bock. Vacuum is then switched to the second channel block, retaining the substrate in proper alignment. This way, accurate registration can be assured between process steps regardless of variation in the dimensions of individual substrates. The transfer block system also maintains alignment of the matrix area during transfers to and from the flow cell during experiments utilizing both mechanical and light-directed process steps.

In some embodiments the channel block need not be utilized. Instead, in some embodiments, small "strips" of reagent are applied to the substrate by, for example, striping the substrate or channels therein with a pipettor. Such embodiments bear some resemblance to the spotting embodiments of this invention. According to other embodiments the channels will be formed by depositing a photoresist such as those used extensively in the semiconductor industry. Such materials include polymethyl methacrylate (PMMA) and its derivatives, and electron beam resists such as poly(olefin sulfones) and the like (more fully described in Ghandi, "VLSI Fabrication Principles," Wiley (1983) Chapter 10, incorporated herein by reference in its entirety for all purposes). According to these embodiments, a resist is deposited, selectively exposed, and etched, leaving a portion of the substrate exposed for coupling. These steps of depositing resist, selectively removing resist and monomer coupling are repeated to form polymers of desired sequence at desired locations.

In some embodiments, a resist can be used to activate certain regions of the substrate. Certain resist materials such as acid-generating polymers, for example, will release protons upon irradiation. According to these embodiments, a substrate covered with such material is irradiated through a mask or otherwise selectively irradiated so that the irradiated regions of the substrate are exposed to acidic conditions. Acid-labile protecting group on the substrate or oligomers on the substrate are removed, leaving an activated region. At this point, all or part of the resist may be removed. In preferred embodiments, the resist will be removed only in the activated regions, so that the channels are formed at the activated regions. Alternatively, the resist can be removed from the entire substrate. In this case, a separate channel block can then be contacted with the substrate to define flow channels, or a conventional VLSIPS™ procedure can be employed.

In preferred embodiments, the substrate is conventional glass, pyrex, quartz, any one of a variety of polymeric materials, or the like. Of course, the substrate may be made from any one of a variety of materials such as silicon, polystyrene, polycarbonate, or the like. In preferred embodiments the channel block is made of silicon or polychlorotrifluorethylene, such as material known under the trade name KelF™ 80 made by 3M, although a wide variety of materials such as polystyrene, polycarbonate, glass, elastomers such as Kalrez made by DuPont, various ceramics, stainless steel, or the like may be utilized.

The channels in the channel block are preferably made by machining, compression molding, injection molding, lithography, laser cutting, or the like depending upon the material of interest. In some embodiments employing larger channel blocks, the raised portions of the channels in the channel block are treated by lapping with lapping film (0.3 μm grit). Such smooth surfaces provide good seals to the substrate without the use of a sealant and, therefore, without the possibility of leaving sealant material on the substrate when rotating the channel block. Preferably, all operations are conducted at substantially ambient temperatures and pressures.

A particularly preferred channel block is prepared by chemical etching of polished silicon wafers. Chemical etching is a widely used technique in integrated circuit fabrications. It can easily provide 60 or more 100 micron channels on a 12.8 mm region of a polished silicon wafer. Even after etching, the top (unetched) surface regions of the wafer retains the very flat profile of the unetched wafer. Thus, close contact with the substrate is ensured during flow cell operation.

In operation, the surface of the substrate is appropriately treated by cleaning with, for example, organic solvents, methylene chloride, DMF, ethyl alcohol, or the like. Optionally, the substrate may be provided with appropriate linker molecules on the surface thereof. The linker molecules may be, for example, aryl acetylene, ethylene glycol oligomers containing from 2-10 monomers or more, diamines, diacids, amino acids, or combinations thereof. Thereafter, the surface is provided with protected surface active groups such as TBOC or FMOC protected amino acids. Such techniques are well known to those of skill in the art.

Thereafter, the channel block and the substrate are brought into contact forming fluid-tight channels bounded by the grooves in the channel block and the substrate. When the channel block and the substrate are in contact, a protecting group removal agent is, thereafter, directed through a first selected channel or group of channels by placing the pipettor on the flow inlet of the selected channel and, optionally, the vacuum source on the outlet of the channel. In the case of, for example, TBOC protected amino acids, this protecting group removal agent may be, for example, trifluoroacetic acid (TFA). This step is optionally followed by steps of washing to remove excess TFA with, for example, dichloromethane (DCM).

Thereafter, a first amino acid or other monomer A is directed through the first selected flow channel. Preferably this first amino acid is also provided with an appropriate protecting group such as TBOC, FMOC, NVOC, or the like. This step is also followed by appropriate washing steps. The of deprotection/coupling steps employed in the first group of channels are concurrently with or thereafter repeated in additional groups of channels. In preferred embodiments, monomer A will be directed through the first group of channels, monomer B will be directed through a second group of flow channels, etc., so that a variety of different monomers are coupled on parallel channels of the substrate.

Thereafter, the substrate and the channel block are separated and, optionally, the entire substrate is washed with an appropriate material to remove any unwanted materials from the points where the channels contact the substrate.

The substrate and/or block is then, optionally, washed and translated and/or rotated with the stage. In preferred embodiments, the substrate is rotated 90 degrees from its original position, although some embodiments may provide for greater or less rotation, such as from 0 to 180 degrees. In other embodiments, such as those discussed in connection with the device shown in FIG. 7, two or more different channel blocks are employed to produce different flow patterns across the substrate. When the channel block is rotated, it may simultaneously be translated with respect to the substrate. "Translated" means any relative motion of the substrate and/or channel block, while "rotation" is intended to refer to rotation of the substrate and/or channel block about an axis perpendicular to the substrate and/or channel block. According to some embodiments the relative rotation is at different angles for different stages of the synthesis.

The steps of deprotection, and coupling of amino acids or other monomers is then repeated, resulting in the formation of an array of polymers on the surface of the substrate. For example, a monomer B may be directed through selected flow channels, providing the polymer AB at intersections of the channels formed by the channel block in the first position with the channels formed by the channel block after 90-degree rotation.

While rotation of the channel block is provided according to preferred embodiments of the invention, such rotation is not required. For example, by simply flowing different reagents through the channels, polymers having different monomer sequences may be formed. Merely by way of a specific example, a portion of the channels may be filled with monomer "A," and a portion filled with monomer "B" in a first coupling step. All or a portion of the first channels are then filled with a monomer "C," and all or a portion of the second channels are filled with a monomer "D," forming the sequences AB and CD. Such steps could be used to form 100 sequences using a basis set of 10 monomers with a 100-groove channel block.

Figure 12:
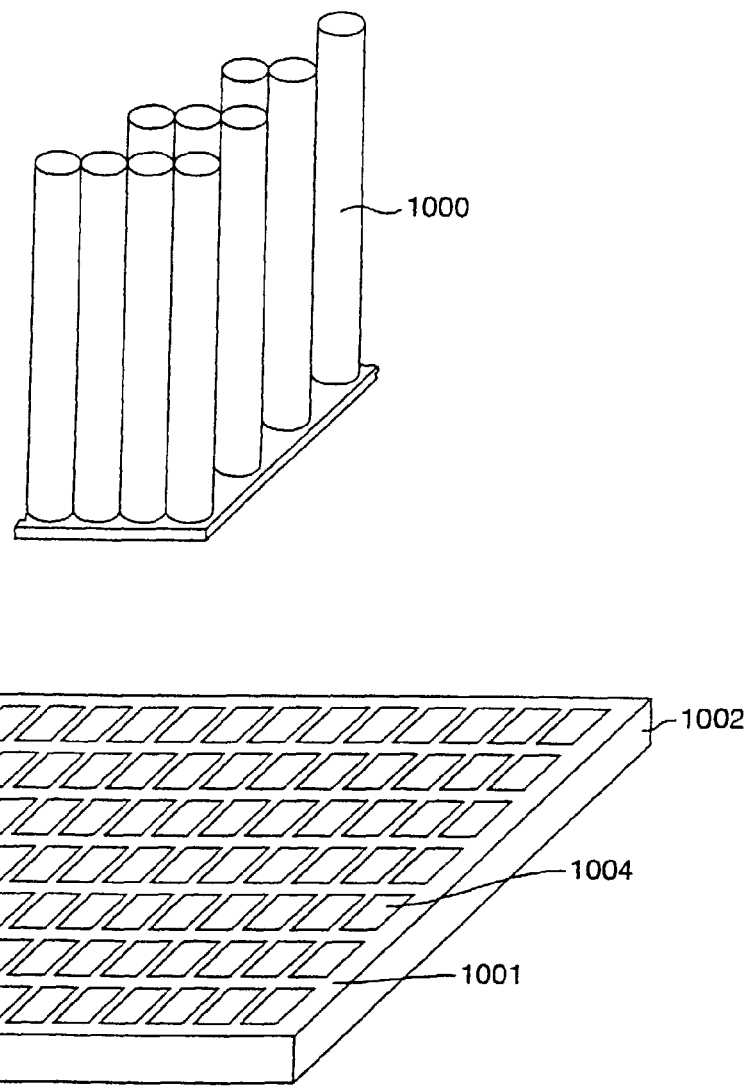
FIG. 12 is a diagram of a multichannel solid-phase synthesizer.

In another embodiment, the invention provides a multichannel solid-phase synthesizer as shown in FIG. 12. In this embodiment, a collection of delivery lines such as a manifold or collection of tubes 1000 delivers activated reagents to a synthesis support matrix 1002. The collection of tubes 1000 may take the form of a rigid synthesis block manifold which can be precisely aligned with the synthesis support matrix 1002. The support matrix contains a plurality of reaction regions 1004 in which compounds may be immobilized or synthesized. In preferred embodiments, the reaction regions include synthesis frits, pads, resins, or the like.

The solutions delivered to the individual reactant regions of the support matrix flow through the reaction regions to waste disposal regions, recycling tank(s), separators, etc. In some embodiments, the reaction solutions simply pass through the reaction regions under the influence of gravity, while in other embodiments, the solutions are pulled or pushed through the reaction regions by vacuum or pressure.

The individual reaction regions 1004 of the support matrix are separated from one another by walls or gaskets 1006. These prevent the reactant solution in one reaction region from moving to and contaminating adjacent reaction regions. In one embodiment, the reaction regions are defined by tubes which may be filled with resin or reaction mixture. The gasketing allows close contact between the support matrix 1002 and a "mask" (not shown). The mask serves to control delivery of a first group reactant solutions through predetermined lines (tubes) to a first set of reaction regions. By ensuring close contact between the delivery tubes 1000, the mask, and the support matrix 1002, the probability that reaction solutions will be accidently added to the wrong reaction site is reduced.

After each process step, the mask can be changed so that a new group reactants is delivered to a new set of reaction regions. In this manner, a combinatorial strategy can be employed to prepare a large array of polymers or other compounds. In other embodiments, mechanisms other than masks can be employed to block the individual delivery tubes. For example, an array of control valves within the tubes may be suitable for some embodiments.

By adjusting the thickness of the synthesis support matrix, the quantity of immobilized material in the reaction regions can be controlled. For example, relatively thin support synthesis matrices can be used to produce small amounts of surface bound oligomers for analysis, while thicker support matrices can be used to synthesize relatively large quantities of oligomers which can be cleaved from the support for further use. In the latter embodiment, a collector having dimensions matching the individual synthesis supports can be employed to collect oligomers that are ultimately freed from the reaction matrix.

To illustrate the ability of this system to synthesize numerous polymers, a square synthesis matrix measuring 10 cm along each side and having 5 mm reaction regions separated by 5 mm wide gaskets provides 100 individual syntheses sites (reaction regions). By reducing the size of the reaction regions to 2.5 mm on each side, 400 reactions regions become available.

Figure 13A:
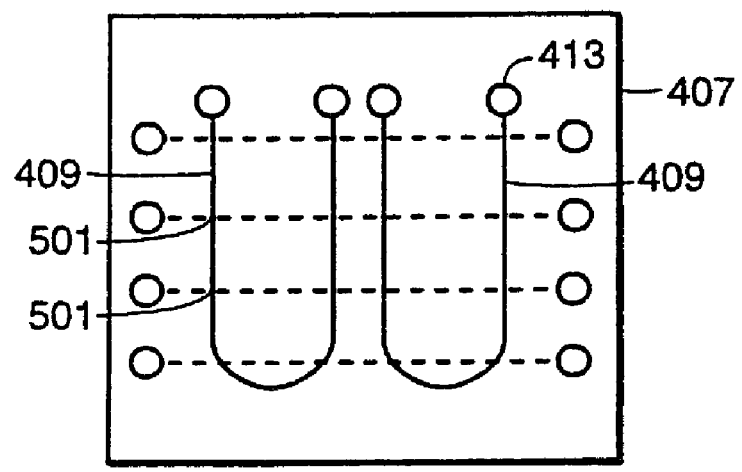
FIGS. 13a and 13b illustrate alternative arrangements of the grooves in a channel block.
Figure 13B:
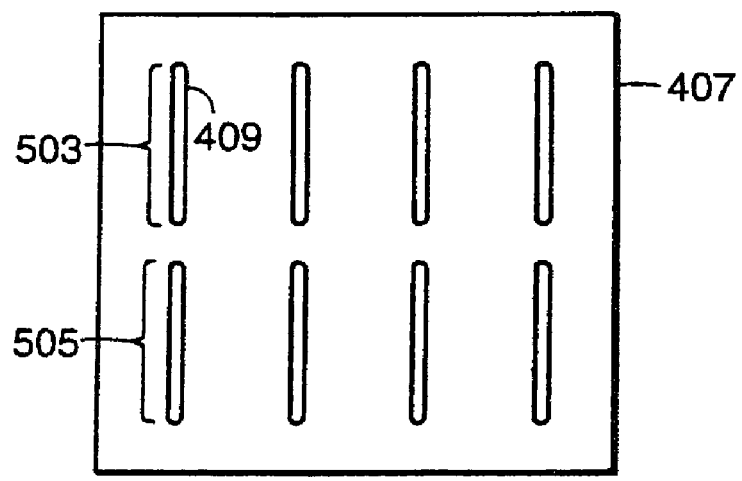

While linear grooves are shown herein in the preferred aspects of the invention, other embodiments of the invention will provide for circular rings or other shapes such as circular rings with radial grooves running between selected rings. According to some embodiments, channel blocks with different geometric configurations will be used from one step to the next, such as circular rings in one step and linear stripes in the next. FIG. 13a illustrates one of the possible arrangements in which the channels 409 are arranged in a serpentine arrangement in the channel block 407. Through appropriate translation and/or rotation of the channel block, polymers of desired monomer sequence are formed at the intersection of the channels during successive polymer additions, such as at location 501, where the intersection of a previous or subsequent set of channels is shown in dashed lines. FIG. 13b illustrates another arrangement in which channels (in this case without flow paths 413) are provided in a linear arrangement, with groups 503 and 505 located in adjacent regions of the substrate and extending only a portion of the substrate length.

In some embodiments of the invention, the various reagents, such as those containing the various monomers, are not pumped through the apertures 413. Instead, the reagent is placed in one of the grooves, such as the grooves 409 shown in FIG. 13b, filling the groove. The substrate is then placed on top of the channel block, and the exposed portions of the substrate are permitted to react with the materials in the grooves. In preferred embodiments, the channels are of the same width as the raised regions between the channels. According to these embodiments, the substrate may then be moved laterally by one channel width or an integer multiple of a channel width, permitting reaction with and placement of monomers on the regions between the channels in a previous coupling step. Thereafter, the substrate or channel block will be rotated for the next series of coupling steps.

In preferred embodiments, the process is repeated to provide more than 10 different polymer sequences on the surface of the substrate. In more preferred embodiments, the process is repeated to provide more than $10^2$, $10^3$, $10^4$, $10^5$, $10^6$, or more polymer sequences on a single substrate. In some embodiments the process is repeated to provide polymers with as few as two monomers, although the process may be readily adapted to form polymers having 3, 4, 5, 6, 10, 15, 20, 30, 40, 50, 75, 100 or more monomers therein.

According to preferred embodiments, the array of polymer sequences is utilized in one or more of a variety of screening processes, one of which is described in copending application U.S. Ser. No. 796,947, filed on Nov. 22, 1991 and incorporated herein by reference for all purposes. For example, according to one embodiment, the substrate is then exposed to a receptor of interest such as an enzyme or antibody. According to preferred embodiments, the receptor is labelled with fluorescein, or otherwise labelled, so as to provide for easy detection of the location at which the receptor binds. According to some embodiments, the channel block is used to direct solutions containing a receptor over a synthesized array of polymers. For example, according to some embodiments the channel block is used to direct receptor solutions having different receptor concentrations over regions of the substrate.

According to most preferred embodiments, amplification of the signal provided by way of fluorescein labelling is provided by exposing the substrate to the antibody of interest, and then exposing the substrate to a labelled material which is complementary to the antibody of interest and which preferably binds at multiple locations of the antibody of interest. For example, in one specific embodiment, if a mouse antibody is to be studied, a labelled second antibody may be exposed to the substrate which is, for example, goat anti-mouse. Such techniques are described in PCT Publication No. WO92/10092, previously incorporated herein by reference.

V. Spotting Embodiments

According to some embodiments, monomers (or other reactants) are deposited from a dispenser in droplets that fill predefined regions. For example, in a single coupling step, the dispenser deposits a first monomer in a series of predefined regions by moving over a first region, dispensing a droplet, moving to a second region, dispensing a droplet, and so on until the each of the selected regions has received the monomer. Next the dispenser deposits a second monomer in a second series of predefined regions in much the same manner. In some embodiments, more than one dispenser may be used so that more than one monomer are simultaneously deposited. The monomers may react immediately on contact with the reaction regions or may require a further activation step, such as the addition of catalyst. After some number of monomers have been deposited and reacted in predefined regions throughout the substrate, the unreacted monomer solution is removed from the substrate. This completes a first process step.

For purposes of this embodiment, the spacing between the individual reaction regions of the substrate preferably will be less than about 3 mm, and more preferably between about 5 and 100 μm. Further, the angular relation between the regions is preferably consistent to within 1 degree and more preferably to within 0.1 degree. Preferably, the substrate will include at least about 100 reaction regions, more preferably at least about 1000 reaction regions, and most preferably at least about 10,000 reaction regions. Of course, the density of reaction regions on the substrate will vary. In preferred embodiments, there are at least about 1000 reaction regions per $cm^2$ of substrate, and more preferably at least about 10,000 regions per $cm^2$.

To deposit reactant droplets consistently at precisely specified regions, a frame of reference common to the delivery instrument and the substrate is required. In other words, the reference coordinates of the instrument must be accurately mapped onto the reference coordinates of the substrate. Ideally, only two reference points on the substrate are necessary to map the array of polymer regions completely. The dispenser instrument locates these reference points and then adjusts its internal reference coordinates to provide the necessary mapping. After this, the dispenser can move a particular distance in a particular direction and be positioned directly over a known region. Of course, the dispenser instrument must provide precisely repeatable movements. Further, the individual regions of the array must not move with respect to the reference marks on the substrate after the reference marks have been formed. Unfortunately, pressing or other mechanical operations commonly encountered during fabrication and use of a substrate can warp the substrate such that the correspondence between the reference marks and the reaction regions is altered.

Thus, in preferred embodiments, a substrate containing both "global" and "local" reference marks is employed. In preferred embodiments, two global reference marks are conveniently located on the substrate to define the initial frame of reference. When these points are located, the dispenser instrument has an approximate map of the substrate and the predefined regions therein. To assist in locating the exact position of the regions, the substrate is further subdivided into local frames of reference. Thus, in an initial, "course" adjustment, the dispenser is positioned within one of the local frames of reference. Once in the local region, the dispensing instrument looks for local reference marks to define further a local frame of reference. From these, the dispenser moves exactly to the reaction region where the monomer is deposited. In this manner, the effects of warpage or other deformation can be minimized. The number of local reference marks is determined by the amount of deformation expected in the substrate. If the substrate is sufficiently rigid so that little or no deformation will occur, very few local reference marks are required. If substantial deformation is expected, however, more local reference marks are required.

In order to locate the appropriate reference point initially and align the dispenser with respect to it, a vision or blind system may be employed. In a vision system, a camera is rigidly mounted to the dispenser nozzle. When the camera locates the reference point(s), the dispenser is known to be a fixed distance and direction away from the point, and a frame of reference is established. Blind systems of the present invention locate the reference point(s) by capacitive, resistive, or optical techniques, for example. In one example of an optical technique, a laser beam is transmitted through or reflected from the substrate. When the beam encounters a reference mark, a change in light intensity is detected by a sensor. Capacitive and resistive techniques are similarly applied. A sensor registers a change in capacitance or resistivity when a reference point is encountered.

Starting at a single reference point, the dispenser is translated from one reaction region to other regions of the substrate by a correct distance in the correct direction (this is the "dead reckoning" navigational technique). At each stop, the dispenser deposits correctly metered amounts of monomer. Analogous systems widely used in the microelectronic device fabrication and testing arts can move at rates of up to 3-10 stops per second. The translational (X-Y) accuracy of such systems is well within 1 μm.

Translational mechanisms for moving the dispenser are preferably equipped with closed loop position feedback mechanisms (encoders) and have insignificant backlash and hysteresis. In preferred embodiments, the translation mechanism has a high resolution, i.e. better than one motor tick per encoder count. Further, the electromechanical mechanism preferably has a high repeatability relative to the reaction region diameter travel distance (typically ±1 μm or better).

To deposit a drop of monomer solution on the substrate accurately, the dispenser nozzle must be placed a correct distance is above the surface. In one embodiment, the dispenser tip preferably will be located about 5-50 μm above the substrate surface when a five nanoliter drop is released. More preferably, the drop will be about 10 μm above the substrate surface when the drop is released. The degree of control necessary to achieve such accuracy is attained with a repeatable high-resolution translation mechanism of the type described above. In one embodiment, the height above the substrate is determined by moving the dispenser toward the substrate in small increments, until the dispenser tip touches the substrate. At this point, the dispenser is moved away from the surface a fixed number of increments which corresponds to a specific distance. From there the drop is released to the cell below. Preferably, the increments in which the dispenser moves less than about 5 μm and more preferably less than about 2 μm.

In an alternative embodiment, the dispenser nozzle is encircled by a sheath that rigidly extends a fixed distance beyond the dispenser tip. Preferably, this distance corresponds to the distance the solution drop will fall when delivered to the selected reaction region. Thus, when the sheath contacts the substrate surface, the movement of the dispenser is halted and the drop is released. It is not necessary in this embodiment to move the dispenser back, away from the substrate, after contact is made. The point of contact with the surface can be determined by a variety of techniques such as by monitoring the capacitance or resistance between the tip of the dispenser (or sheath) and the substrate below. A rapid change in either of these properties is observed upon contact with the surface.

To this point, the spotting system has been described only in terms of translational movements. However, other systems may also be employed. In one embodiment, the dispenser is aligned with respect to the region of interest by a system analogous to that employed in magnetic and optical storage media fields. For example, the region in which monomer is to be deposited is identified by a track and sector location on the disk. The dispenser is then moved to the appropriate track while the disk substrate rotates. When the appropriate cell is positioned below the dispenser (as referenced by the appropriate sector on the track), a droplet of monomer solution is released.

Control of the droplet size may be accomplished by various techniques. For example, in one embodiment, a conventional micropipetting instrument is adapted to dispense droplets of five nanoliters or smaller from a capillary. Such droplets fit within regions having diameters of 300 μm or less when a non-wetting mask of the invention is employed.

In another embodiment, the dispenser is a piezoelectric pump that generates charged droplets and guides them to the reaction region by an electric field in a manner analogous to conventional ink-jet printers. In fact, some ink-jet printers can be used with minor modification by simply substituting a monomer containing solution for ink. For example, Wong et al., European Patent Application 260 965, incorporated herein by reference for all purposes, describes the use of a commercial printer to apply an antibody to a solid matrix. In the process, a solution containing the antibody is forced through a small bore nozzle that is vibrating in a manner that fragments the solution into discrete droplets. The droplets are subsequently charged by passing through an electric field and then deflected onto the matrix material.

A conventional ink drop printer includes a reservoir in which ink is held under pressure. The ink reservoir feeds a pipe which is connected to a nozzle. An electromechanical transducer is employed to vibrate the nozzle at some suitable high frequency. The actual structure of the nozzle may have a number of different constructions, including a drawn glass tube which is vibrated by an external transducer, or a metal tube vibrated by an external transducer (e.g. a piezoelectric crystal) or a magnetostrictive metal tube which is magnetostrictively vibrated. The ink accordingly is ejected from the nozzle in a stream which shortly thereafter breaks into individual drops. An electrode may be present near the nozzle to impart a charge to the droplets. Conventional ink drop dispensers are described in U.S. Pat. Nos. 3,281,860 and 4,121,222, which are incorporated by reference herein for all purposes.

In a different preferred embodiment, the reactant solutions are delivered from a reservoir to the substrate by an electrophoretic pump. In this device, a thin capillary connects a reservoir of the reactant with the nozzle of the dispenser. At both ends of the capillary, electrodes are present to provide a potential difference. As is known in the art, the speed at which a chemical species travels in a potential gradient of an electrophoretic medium is governed by a variety of physical properties, including the charge density, size, and shape of the species being transported, as well as the physical and chemical properties of the transport medium itself. Under the proper conditions of potential gradient, capillary dimensions, and transport medium rheology, a hydrodynamic flow will be set up within the capillary. Thus, in an electrophoretic pump of the present invention, bulk fluid containing the reactant of interest is pumped from a reservoir to the substrate. By adjusting the appropriate position of the substrate with respect to the electrophoretic pump nozzle, the reactant solution is precisely delivered to predefined reaction regions.

In one particularly useful application, the electrophoretic pump is used to produce an array containing various fractions of an unknown reactant solution. For example, an extract from a biological material such as leaf or a cell culture might contain various unknown materials, including receptors, ligands, alkaloids, nucleic acids, and even biological cells, some of which may have a desired activity. If a reservoir of such extract is electrophoretically pumped, the various species contained therein will move through the capillary at different rates. Of course, the various components being pumped should have some charge so that they can be separated. If the substrate is moved with respect to the dispenser while the extract components are being separated electrophoretically, an array containing various independent species is produced. This array is then tested for activity in a binding assay or other appropriate test. Those elements of the array that show promising activity are correlated with a fraction of the extract which is subsequently isolated from another source for further study. In some embodiments, the components in the extract solution are tagged with, for example, a fluorescent label. Then, during the process of delivering the solution with the electrophoretic pump, a fluorescence detector determines when labeled species are being deposited on the substrate. In some embodiments, the tag selectively binds to certain types of compounds within the extract, and imparts a charge to those compounds.

Other suitable delivery means include osmotic pumps and cell (biological) sorters. An osmotic pump delivers a steady flow of solution for a relatively long period. The construction of such pumps is well-known in the art, generally incorporating a solution of the extract of interest within a solvent permeable bag. Osmotic pressure is applied to the extract solution by solvent molecules diffusing across the bag to equalize a concentration difference. The extract is thus forced out of a nozzle in the bag at a constant rate. Cell sorters are also well-known in the art, and can be used in applications where it is desirable to apply single biological cells to distinct locations on the substrate.

Although the above embodiments have been directed to systems employing liquid droplets, minuscule aliquots of each test substance can also be delivered to the cell as miniature pellets. Such pellets can be formed from the compound of interest (e.g. ligands for use in an affinity assay) and one or more kinds of inert binding material. The composition of such binders and methods for the preparation of the pellets will be apparent to those of skill in the art. Such "mini-pellets" will be compatible with a wide variety of test substances, stable for long periods of time, suitable for easy withdrawal from the storage vessel and dispensing (i.e., non-tacky, preferably suspendable in a liquid such as physiological buffer), and inert with respect to the binding activity of receptors.

In preferred embodiments, the reactant solutions in each predefined region are prevented from moving to adjacent regions by appropriate barriers or constraining regions. For example to confine aqueous monomer solutions, a hydrophilic material is used to coat the reaction regions, while a hydrophobic material is used in preferred embodiments to coat the region surrounding the individual reaction regions. Of course, when non-aqueous or nonpolar solvents are employed, different surface coatings are generally preferred. By choosing appropriate materials (substrates, hydrophobic coatings, and reactant solvents), the contact angle between the droplet and the substrate is advantageously controlled. Large contact angles between the reactant droplets and the substrate are desired because the solution then wets a relatively small reaction region with shallow contact angles, on the other hand, the droplet wets a larger area. In extreme cases, the droplet will spread to cover the entire surface.

The contact angle is determined by the following expression, known as Young's equation:

$$\cos \theta = (\sigma_{sa} - \sigma_{sl})/\sigma_{la}$$

where $\theta$ is the wetting angle, $\sigma_{sa}$ is the solid-air tension, $\sigma_{sl}$ is the solid-liquid tension, and $\sigma_{la}$ is the liquid-air surface tension. The values of these surface tensions are governed by thermodynamic considerations including the chemical constituents of the liquid and the solid substrate. The liquid-air surface tension for various chemicals is easily measured by a variety of techniques such as those described in Adamson, *Physical Chemistry of Surfaces*, John Wiley and Sons, 5th Ed. (1990) which is incorporated herein by reference for all purposes. The difference of the solid-liquid and solid-air tensions can, for a given system, be determined empirically from a Zisman plot. In this approach, the contact angles are measured for a homologous series of liquids on a given solid surface. For some liquid in the series, a "critical contact angle" is observed, beyond which lower surface tension liquids wet the surface. The liquid-air surface tension of the liquid at this critical contact angle is assumed to be the surface tension of the solid. This approach has been found to provide quite reasonable results for low energy solids such as Teflon, polyethylene, hydrocarbons, etc. The information gained from such studies is used to optimize substrate compositions to increase wetting angles for given reactant solutions in the array.

Methods for controlling chemical composition and therefore the local surface free energy of a substrate surface include a variety of techniques apparent to those skilled in the art. Chemical vapor deposition and other techniques applied in the fabrication of integrated circuits can be applied to deposit highly uniform layers on selected regions of a surface. As a specific example, the wettability of a silicon wafer surface has been manipulated on the micrometer scale through a combination of self-assembled monolayer depositions and micromachining. See Abbott et al., "Manipulation of the Wettability of Surfaces on the 0.1 to 1 Micrometer Scale Through Micromachining and Molecular Self-Assembly" Science, 257 (Sep. 4, 1992) which is incorporated herein by reference for all purposes.

In a preferred embodiment, the perimeters of the individual regions are formed on a hydrophilic substrate defined by selectively removing hydrophobic protecting groups from the substrate surface. For example, a mono-layer of hydrophobic photoprotecting groups can be coupled to, for example, linker molecules attached to the substrate surface. The surface then is selectively irradiated (or otherwise activated by, for example, acid) through a mask to expose those areas where the reaction regions are to be located. This cleaves the protecting groups from the substrate surface, causing the reaction regions to be less hydrophobic than the surrounding area. This process produces a high density of reaction regions on the substrate surface. Because hydrophobic materials have lower surface free energies (surface tensions) than water, the solution droplet in the cell beads rather than spreads.

In some preferred embodiments, the substrate is prepared by first covalently attaching a monolayer of the desired reactive functional group (e.g. amine, hydroxyl, carboxyl, thio, etc.), which is protected by a hydrophobic photolabile protecting moiety. If the substrate provides a glass surface, the monolayer may be deposited by a silanation reaction as shown below

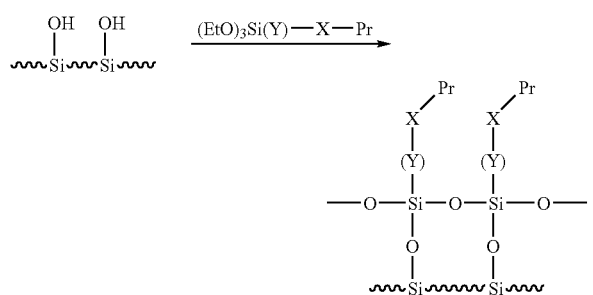

In the above structures, Y is a spacer group such as a polymethylene chain, X is a reactive protected group such as NH, C(O)O, O, S, etc., and Pr is a hydrophobic photolabile protecting group.

In an alternative preferred embodiment shown below, the substrate surface is first derivatized by, for example, a silanation reaction with appropriates to provide an amine layer. A molecule including a spacer, a reactive group, and a photolabile group is then coupled to the surface.

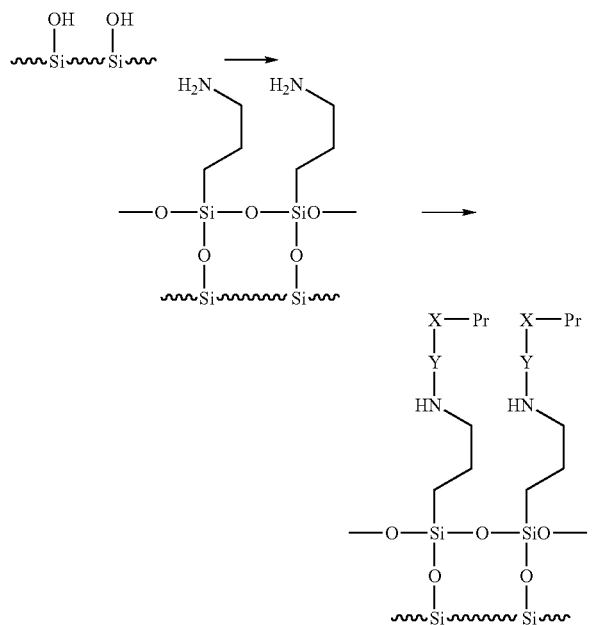

The photolabile protecting group should be sufficiently hydrophobic as to render the substrate surface substantially non-wettable. Removal of the protecting group in specific areas by exposure to light through a suitable mask, liberates the reactive functional groups. Because these groups are hydrophilic in character, they will render the substrate wettable in the exposed regions.

Figure 14:
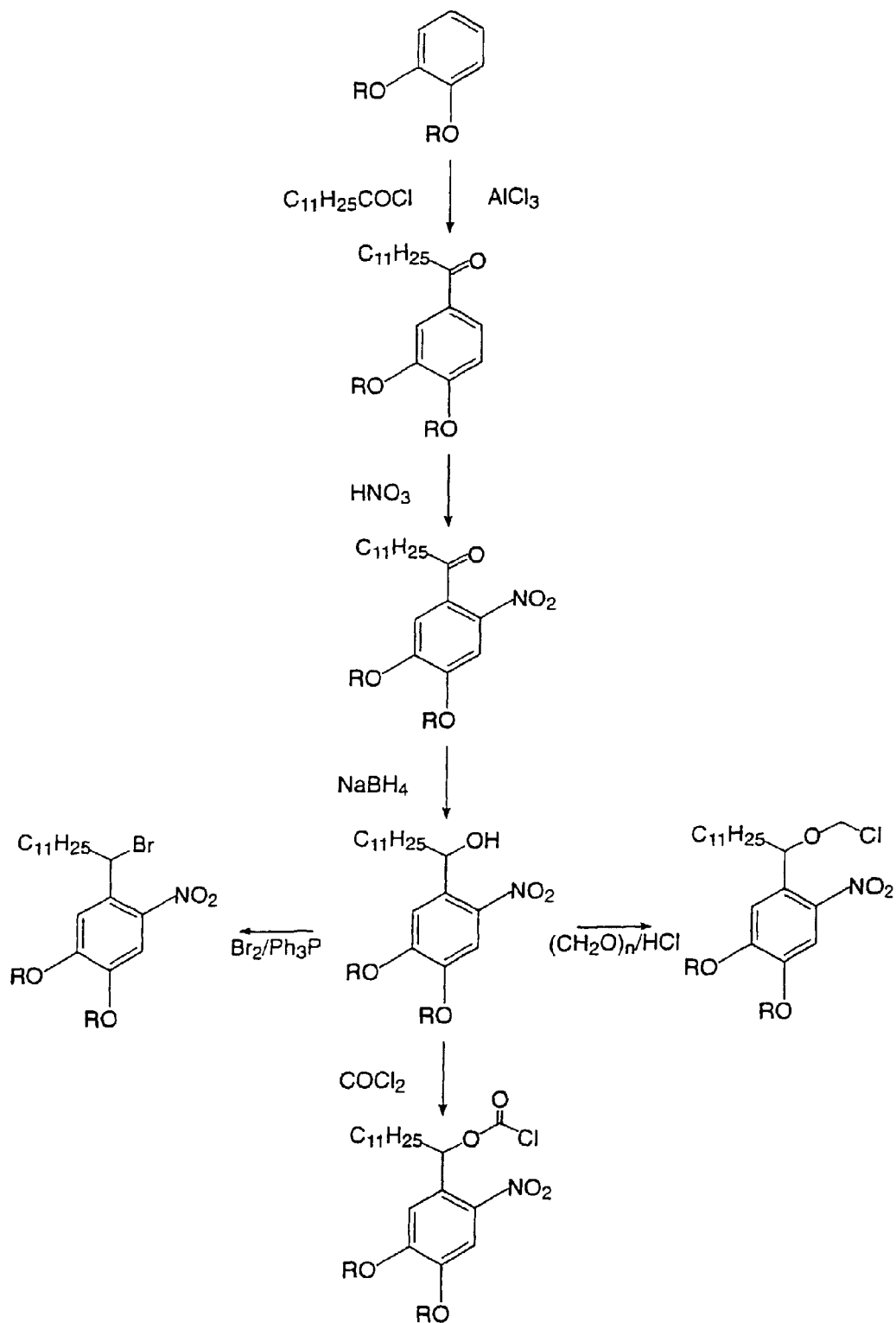
FIG. 14 is a schematic illustration of reaction pathways used to prepare some hydrophobic groups of the present invention.

The class of nitrobenzyl protecting groups, which is exemplified by the nitroveratryl group, imparts significant hydrophobicity to glass surfaces to which a member of the class is attached. The hydrophobicity of the basic nitrobenzyl protecting group is enhanced by appending group chain hydrocarbon substituent. Exemplary hydrophobic chains include $C_{12}H_{25}$ (lauryl) or $C_{18}H_{37}$ (stearyl) substituents. The syntheses of suitably activated forms (bromide, chloromethyl ether, and oxycarbonyl chloride) of a typical protecting group is schematically outlined in FIG. 14.

The spacer group ("Y") contributes to the net hydrophobic or hydrophilic nature of the surface. For example, those spacers consisting primarily of hydrocarbon chains, such as $—(CH_2)_n—$, tend to decrease wettability. Spacers including polyoxyethylene $(—(CH_2CH_2O)_n—)$, or polyamide $(—(CH_2CONH)_n—)$ chains tend to make the surface more hydrophilic. An even greater effect is achieved by using spacer groups which possess, in addition to the protected functional group, several "masked" hydrophilic moieties. This is illustrated below.

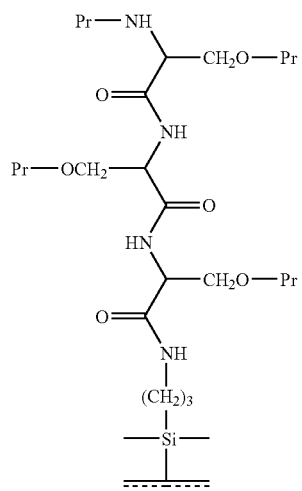

In preferred embodiments, the hydrophilic reaction regions is a two-dimensional circle or other shape having an aspect ratio near one (i.e. the length is not substantially larger or smnaller than the width). However, in other embodiments, the hydrophilic region may take the form of a long channel which is used to direct flowing reactants in the manner described above.

In still other embodiments, the reaction regions are three-dimensional areas defined by, for example, gaskets or dimples on the substrate surface. The dimples or gaskets may also act as identification marks directing the dispenser to the region of interest.

If the solvent (or other liquid used to deliver the reactant) has a sufficiently high vapor pressure, evaporation can cause the reactant concentration to increase. If left unchecked, this process ultimately causes the solute to precipitate from solution. The effects of evaporation can be minimized by sealing selected regions of the substrate when they need not be accessible. Alternatively, the partial pressure of volatile reagents can be adjusted so that the liquid and vapor phase fugacities are equalized and the thermodynamic force driving evaporation is reduced. The partial pressure of the reagents may be increased by providing a relatively large reservoir of volatile reagents in a sealed chamber. For example, solvents having a low vapor pressure under the conditions of interest can be used. In some cases, evaporation can be further controlled by application of a film or coverplate having a reverse array pattern. Other methods of preventing evaporation are well-known in the physical chemical arts and may be used in the present invention.

In some preferred embodiments, evaporation is advantageously employed to accelerate hybridization of target oligonucleotides with immobilized oligonucleotides in the reaction regions. In one specific embodiment, fluorescently tagged or otherwise labelled target oligonucleotides in solution (e.g., a solution containing a salt such as ammonium acetate or magnesium chloride) are delivered to reaction regions containing immobilized probe oligonucleotides. As the volatile salt solution evaporates from the reactant droplet (in the same manner as solvent evaporates from an ink droplet deposited by an ink jet printer), a locally high concentration ratio of target to probe oligonucleotide results, accelerating hybridization. If hybridization is carried out at room temperature, ten minutes to a few hours are typically required to complete the reaction. After sufficient time, the unhybridized DNA is washed or otherwise removed from the substrate. Finally, the substrate is imaged to detect regions in which the probe and target DNA have hybridized. Of course, evaporation can be advantageously employed to increase the local concentration of non-DNA solutes in a variety of reactions besides hybridization. For example in some embodiments, receptor solutions are sufficiently volatile that the local receptor concentration increases in the reaction regions containing peptides, for example, to be screened.

The arrays produced according to the above spotting embodiments are generally used in much the same manner as the arrays produced by the flow channel embodiments described above. For example, the arrays can be used in screening with fluorescein labelled receptors as described in PCT Publication No. WO92/10092, previously incorporated by reference.

VI. Alternative Embodiments

According to some embodiments of the invention, microvalve structures are used to form channels along selected flow paths on the substrate. According to these embodiments, an array of microvalves is formed and operated by an overlying or underlying array of electrodes that is used to energize selected valves to open and close such valves.

Figure 15A:
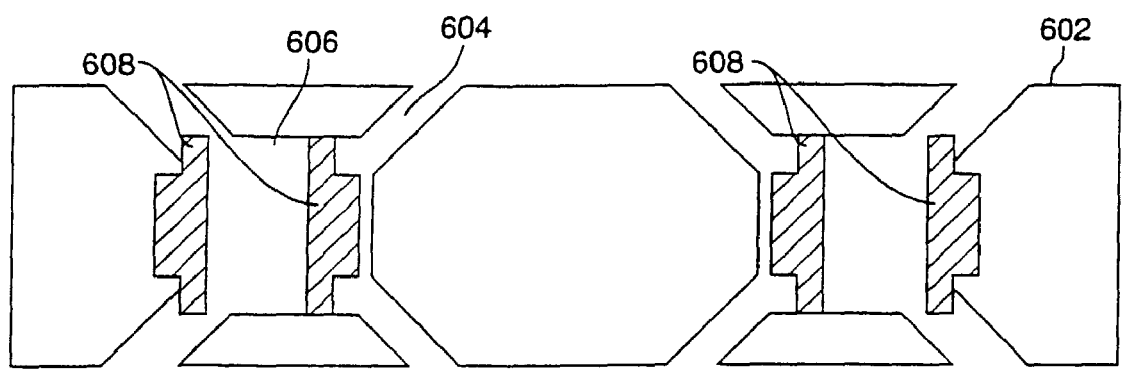
FIGS. 15a and 15b illustrate a microvalve device.
Figure 15B:
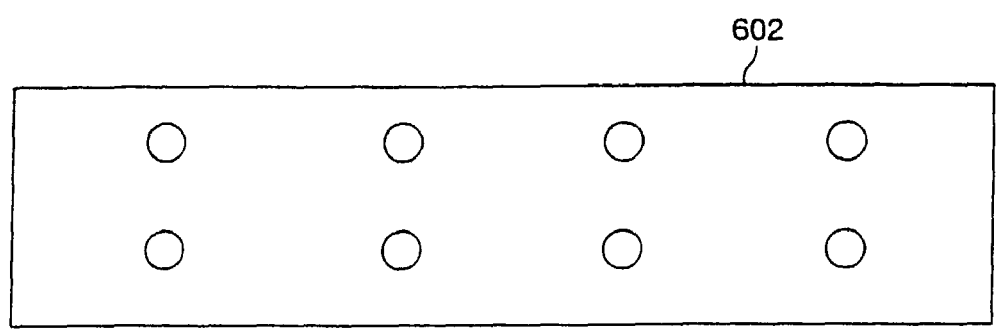

FIG. 15 illustrates such a structure, FIG. 15a illustrating the system in end view cross-section and FIG. 15b illustrating the system in top view. The structure shown therein provides for only two synthesis chambers for the purpose of clarity, but in most embodiments a far greater number of chambers will be provided. Microvalves are discussed in detail in, for example, Zdeblick, U.S. Pat. No. 4,966,646, and Knutti, "Advanced Silicon Microstructures," ASICT Conference (1989), both incorporated herein by reference for all purposes.

As shown therein, a substrate 602 is provided with a plurality of channels 604 formed using photolithographic, or other related techniques. The channels lead up to a synthesis chamber 606. At the end of each channel is valve structure 608. As shown in FIG. 15, the channels lead up to the chambers, but may be isolated from the chambers by the valves. Multiple valves may be provided for each chamber. In the particular structure shown in FIG. 15, the right valve on the left chamber and the left valve on the right chamber are open while the remaining valves are closed. Accordingly, if reagent is delivered to the top of the substrate, it will flow through the open channel to and through the chamber on the left, but not the one on the right. Accordingly, coupling steps may be conducted on the chamber with selected reagents directed to selected chambers, using the techniques discussed above.

According to some embodiments, a valve is supplied on one side of the chamber 606, but the valve on the opposite side is replaced by a semi-permeable membrane. According to these embodiments, it becomes possible to flow a selected reagent into the chamber 606 and, thereafter, flow another selected reagent through the flow channel adjacent the semi-permeable membrane. The semi-permeable membrane will permit a portion of the material on one side or the other to pass through the membrane. Such embodiments will be useful in, for example, cell studies.

Screening will be performed by, for example, separating or cutting two halves of the device, enabling screening by, for example, contacting with a fluorescein labelled antibody, or the like followed by photodetection.

Figure 16A:
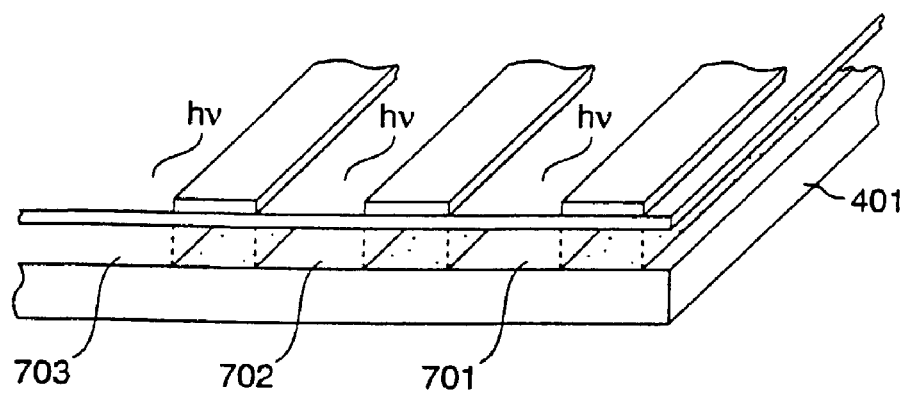
FIGS. 16a and 16b illustrate an alternative embodiment of the invention.
Figure 16B:
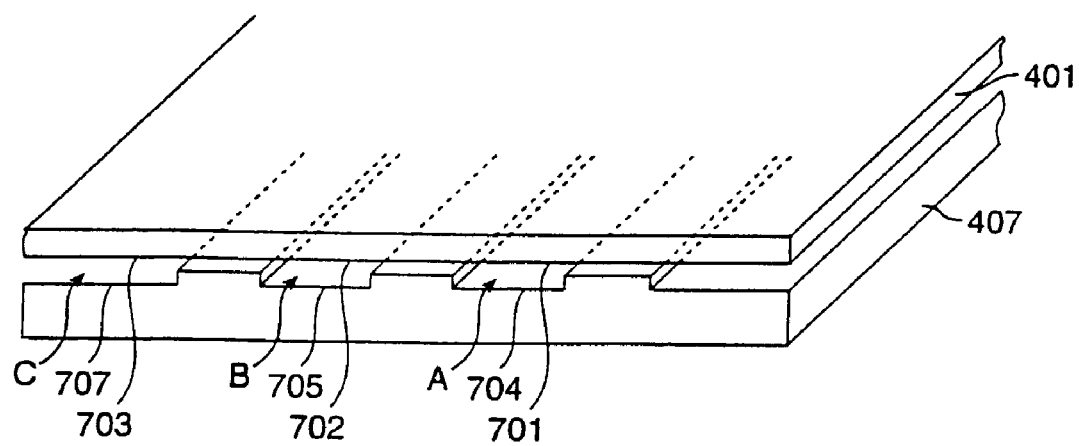

FIGS. 16a and 16b illustrate another alternative embodiment of the invention which combines the mechanical polymer synthesis techniques disclosed herein with light-directed synthesis techniques. According to these embodiments, a substrate 401 is irradiated in selected regions, shown as the stripes in FIG. 16a. The surface of the substrate is provided with photoremovable groups in accordance with PCT Publication No. WO92/10092 (previously incorporated by reference) on, for example, amine groups in the specific case of peptide synthesis. During this step regions 701, 702, and 703 of the substrate, among others, are deprotected, leaving remaining regions of the substrate protected by photoremovable groups such as nitroveratryl oxycarbonyl ("NVOC"). According to a specific embodiment of the invention, the widths of the irradiated regions equal the widths of the protected regions of the substrate.

Thereafter, as shown in FIG. 16b the substrate is contacted with a channel block 407. In the particular embodiment shown in FIG. 16b, the channels 704, 705, and 707 are aligned with the regions 701, 702, and 703, respectively, on the substrate 401. As will be apparent, specific embodiments of the invention provide for irradiated regions and channels in the form of stripes, which are aligned during this step. Other embodiments, however, will provide for other shapes of irradiated regions and channels, and other relative orientations of the irradiated regions and channels. The channel block and substrate will be aligned with, for example, an alignment mark placed on both the substrate and the channel block. The substrate may be placed on the channel block with, for example, a vacuum tip.

Thereafter, a selected reagent is flowed through or placed in the channels in the channel block for coupling to the regions which have previously been exposed to light. As with the flow channel embodiments described above, the substrate may be placed in contact with a prefilled channel block in some embodiments to avoid compression of the channel block to the substrate and dead spots during pumping. According to preferred aspects of the invention, a different reagent flows through each of the channels 701, 702, and 703 such as, for example, a reagent containing monomers A, B, and C. The process may then, optionally, involve a second coupling step in which the substrate is translated by, e.g., one channel width, to provide coupling of a monomer in the regions between the original channels.

Thereafter, the process of directed irradiation by light, followed by coupling with the channel block is repeated at the previously unexposed regions. The process is then preferably repeated again, with the stripes of the mask and the channel block rotated at, for example, 90 degrees. The coupling steps will provide for the formation of polymers having diverse monomer sequences at selected regions of the substrate through appropriate translation of the mask and substrate, and through appropriate mask selection. Through a combination of the light-directed techniques and the mechanical flow channel techniques disclosed herein, greater efficiency in forming diverse sequences is achieved, because multiple monomers are coupled in a single irradiation/coupling step.

In light-directed methods, the light shown through the mask is diffracted to varying degrees around the edges of the dark regions of the mask. Thus, some undesired removal of photosensitive protecting groups at the edges of "dark" regions occurs. This effect is exacerbated by the repeated mask translations and subsequent exposures, ultimately leading to inhomogeneous synthesis sites at the edges of the predefined regions. The effect is, of course, dependent upon the thickness of the glass substrate and the angle at which the light is diffracted. If the mask is positioned on the "backside" of the substrate, a diffraction angle of 2.5° and a substrate thickness of 0.7 mm creates a 60 µm strip of light (of variable intensity) flanking each edge. For a 0.1 mm thick substrate, the strip is approximately 5 µm wide.

To reduce these "bleed-over" effects of diffraction, a pinhole mask may be employed to activate and/or define reaction regions of the substrate. Thus, for example, light shown through the pinhole mask is directed onto a substrate containing photoremovable hydrophobic groups. The groups in the illuminated regions are then removed to define hydrophilic reaction regions. In one specific embodiment, the pinhole mask contains a series of circular holes of defined diameter and separation, e.g., 20 µm diameter holes spaced 50 µm apart. In some preferred embodiments, a stationary pinhole mask is sandwiched between the substrate and a translational mask of the type described in PCT Publication No. WO92/10092. In this manner selected regions of the substrate can be activated for polymer synthesis without bleed-over. The translational mask is used to illuminate selected holes of the stationary pinhole mask, and is aligned such that its edges dissect the distance separating the holes of the stationary mask thereby eliminating diffractive removal of photoprotecting groups at neighboring sites. Because there is negligible bleed-over incident light, inhomogeneous synthesis at sites juxtaposed along the edge is eliminated. The resulting circular sites do, of course, contain variable sequence density due to diffraction at the edges of the pinhole mask, but the sequences at each predefined region are homogeneous. In addition, each synthesis region is surrounded by a "dark" region when the substrate is probed with a labeled target. Thus, no bleed-over fluorescence signal is introduced by binding at neighboring sites.

A pinhole mask containing 20 µm circular holes separated by 50 µm requires a total synthesis area for the complete set of octanucleotides of only 1.78 cm². For a given pinhole mask, thinner substrates allow for smaller reaction sites separated by larger distances. However, the area from which reliable data can be obtained is also reduced when smaller sites are used. The density of reaction sites is ultimately determined by the diffraction angle and the distance between the pinhole mask and the reaction regions (typically the substrate thickness).

Although the discussion so far has focused upon circular pinholes, other shapes such as slots, squares, crescents, etc. may be employed as is appropriate for the selected delivery method. Thus, for some flow channel embodiments, linear or serpentine slots may be desired.

In alternative preferred embodiments, the pinhole mask takes the form of a layer coated on the substrate. This avoids the need for a separate stationary mask to generate the dot pattern. In addition, the surface layer provides well defined synthesis regions in which to deposit reactants according to the spotting embodiments described above. Further, the surface pinhole mask is conveniently embossed with local reference coordinates for use in navigational systems used to deliver monomer solutions to proper regions as described above. Preferred pinhole masks are made from opaque or reflective materials such as chrome.

VI. Examples

A. Leak Testing

An initial experiment was conducted using a flow channel device to ensure that solutions could be delivered to selected locations of a substrate and be prevented from contacting other areas. Additionally, the experiment was used to demonstrate that reagents could be delivered in a uniform manner.

Accordingly, a flat piece of conventional glass having dimensions of about 42 mm×42 mm was derivatized with aminopropyltriethoxysilane. The entire slide was deprotected and washed using conventional techniques. A fluorescein marker of FITC was then injected into flow channels formed when a block of KelF™ 81 with 10 channels of 1 mm depth and 1 mm width were brought into contact with the substrate. The fluorescein marker was in a solution of DMF and flowed through the channels by injecting the material into the groove with a manual pipet.

Figure 17:
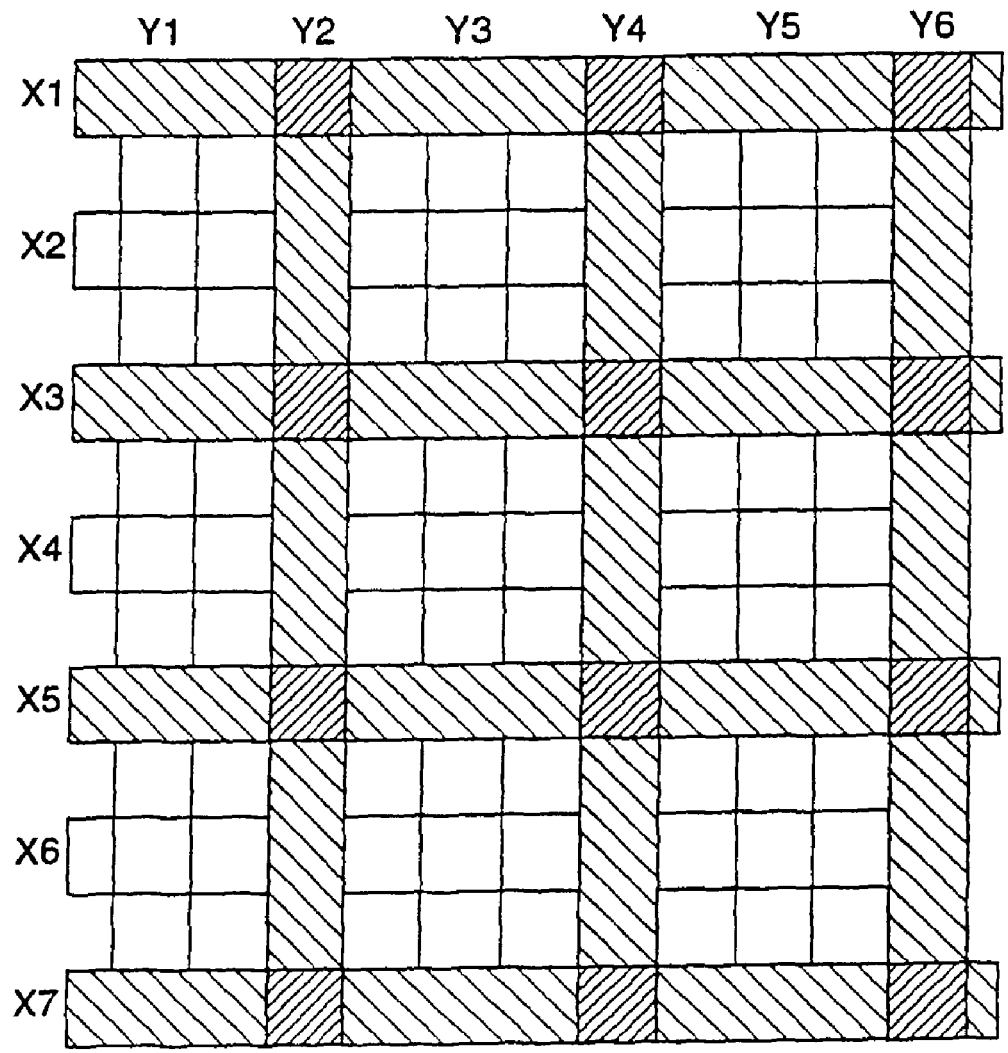
FIG. 17 is a mapping of expected fluorescent intensities with a substrate selectively exposed to fluorescent dye.

Fluorescein dye was similarly injected into every other channel in the block, the block was rotated, and the process was repeated. The expected resulting plot of fluorescent intensity versus location is schematically illustrated in FIG. 17. Dark regions are shown at the intersections of the vertical and horizontal stripes, while lighter grey at non-intersecting regions of the stripes. The dark grey regions indicate expected regions of high dye concentration, while the light regions indicate regions of expected lower dye concentration.

Figure 18:
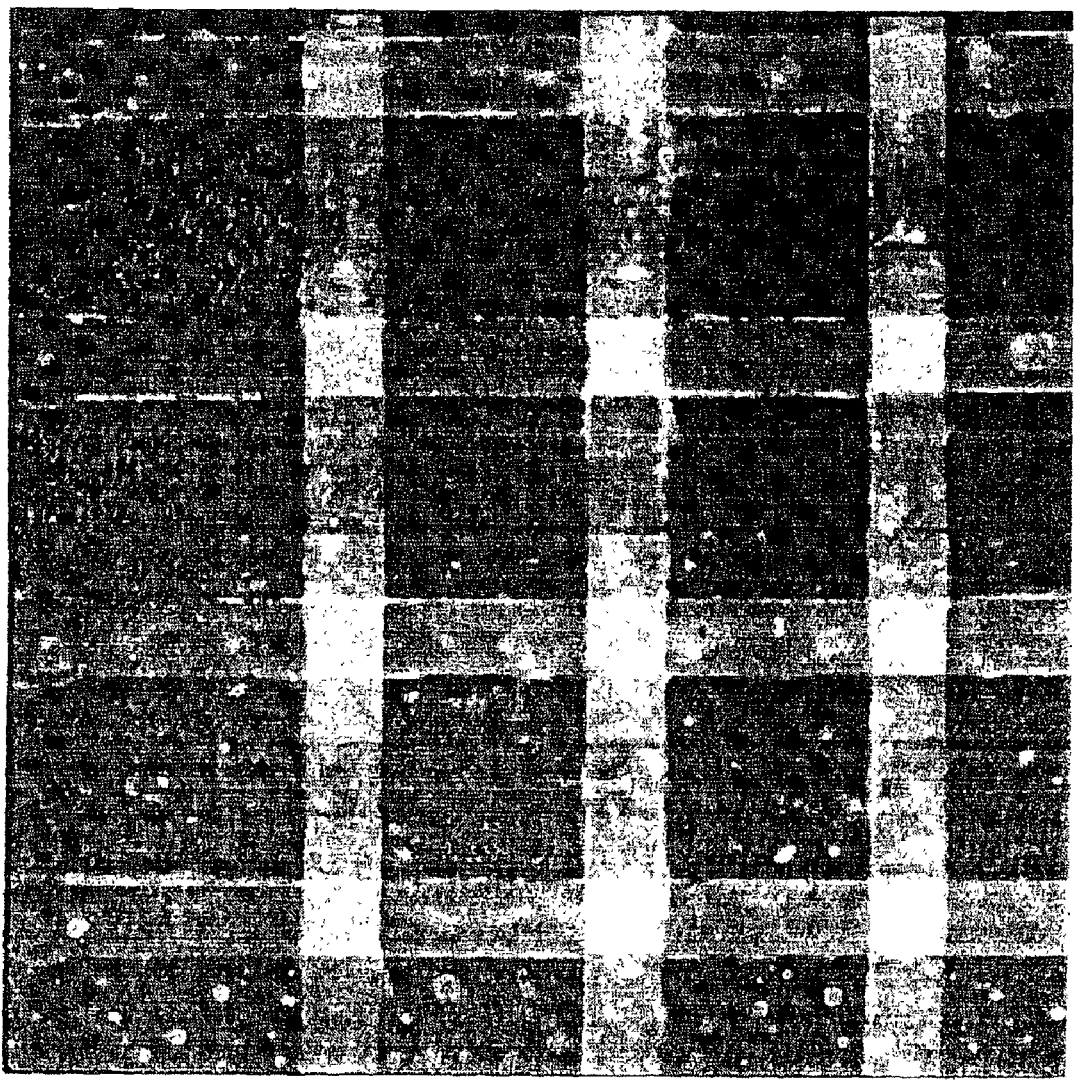
FIG. 18 is a mapping of actual fluorescence intensity versus location.

FIG. 18 is a mapping of fluorescence intensity of a portion of an actual slide, with intensity data gathered according to the methods of PCT Publication No. WO92/10092, previously incorporated by reference. The results agree closely with the expected results, exhibiting high fluorescence intensity at the intersection of the channels (about 50% higher than non-intersecting regions of the stripes), and lower fluorescence intensity at other regions of the channels. Regions which were not exposed to fluorescence dye show little activity, indicating a good signal-to-noise ratio. Intersections have fluorescence intensity about 9× as high as background. Also, regions within the channels show low variation in fluorescence intensity, indicating that the regions are being evenly treated within the channels.

B. Formation of YGGFL (SEQ. ID NO:1)

The system was used to synthesize four distinct peptides: YGGFL (SEQ. ID NO:1), YpGFL (SEQ. ID NO:2), pGGFL (SEQ. ID NO:3), and ppGFL (SEQ. ID NO:6) (the abbreviations are included in Stryer, Biochemistry, Third Ed. (1988), previously incorporated herein by reference; lower case letters indicate D-optical isomers and upper case letters indicate L-optical isomers). An entire glass substrate was derivatized with TBOC-protected aminopropyltriethoxysilane, deprotected with TFA, coated with FMOC-protected caproic acid (a linker), deprotected with piperidine, and coated with FMOC-protected Glycine-Phenylalanine-Leucine (GFL).

This FMOC-GFL-coated slide was sealed to the channel block, and all 10 grooves were deprotected with piperidine in DMF. After washing the grooves, FMOC Glycine (G) was injected in the odd grooves, and FMOC d-Proline (p) was injected in the even grooves. After a two-hour coupling time, using standard coupling chemistry, all grooves were washed with DMF. The grooves were vacuum dried, the block removed and rotated 90 degrees. After resealing, all grooves were deprotected with piperdine in DMF and washed. FMOC Tyrosine (Y) was injected in the odd grooves, and FMOC p in the even grooves. After coupling the grooves were washed and vacuum dried. Accordingly, 25 regions of each of the compounds YGGFL (SEQ. ID NO:1), YpGFL (SEQ. ID NO:2), pGGFL (SEQ. ID NO:3), and ppGFL (SEQ. ID NO:6) were synthesized on the substrate. The substrate was removed and stained with FITC-labelled antibodies (Herz antibody 3E7).

Figure 19:
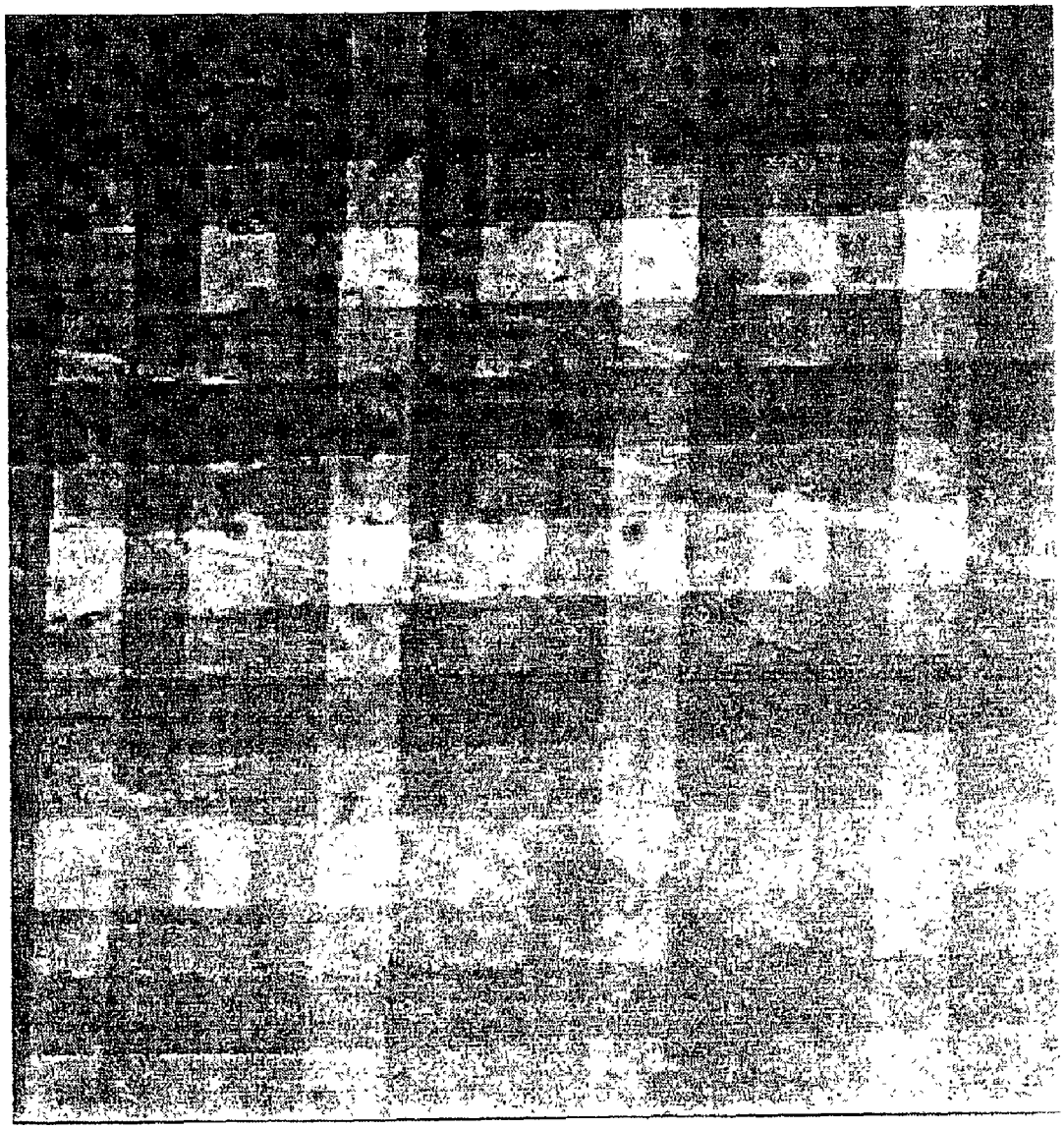
FIG. 19 is a mapping of fluorescence intensity versus location on a slide having four different peptides synthesized thereon.

A section of the resulting slide illustrating fluorescence intensity is shown in FIG. 19. White squares are in locations of YGGFL (SEQ. ID NO:1). The darkest regions are pGGFL (SEQ. ID NO:3) and ppGFL (SEQ. ID NO:6). The YGGFL (SEQ. ID NO:1) sites were the most intense, followed by the YpGFL (SEQ. ID NO:2) sites. The pGGFL (SEQ. ID NO:3) and ppGFL (SEQ. ID NO:6) intensities were near background levels, consistent with expected results with the Herz antibody.

Quantitative analysis of the results show overall intensity ratios for YGGFL (SEQ. ID NO:1):YpGFL (SEQ. ID NO:2): pGGFL (SEQ. ID NO:3):ppGFL (SEQ. ID NO:6) as 1.7:1.5: 1.1:1.0. However, since there is a large standard deviation on the YGGFL (SEQ. ID NO:1) and YpGFL (SEQ. ID NO:2), comparing all the sites with each other may not accurately represent the actual contrasts. Comparing the intensities of sites within the same "stripe" gives larger contrasts, although they remain on the order of 2:1.

C. 100 Micron Channel Block

A grid pattern of fluorescein isothiocyanate coupled to a substrate was made by using a flow cell of this invention. A two by three inch NVOC-derivatized substrate was photolyzed through a mask to produce 400 micron activated bands on one axis. An etched silicon channel block having 64 parallel 100 micron channels separated by 100 micron walls was then clamped to the substrate on the other axis (i.e., perpendicular to the axis of 400 micron activated bands). The clamping assembly consisting of aluminum top and bottom clamp plates was used. Pressure was applied by tightening two bolts with a torque wrench to 400 psi. A 7 mM fluorescein isothiocyanate solution was flowed through the channels by pipetting directly to exposed channel ends.

Figure 20:
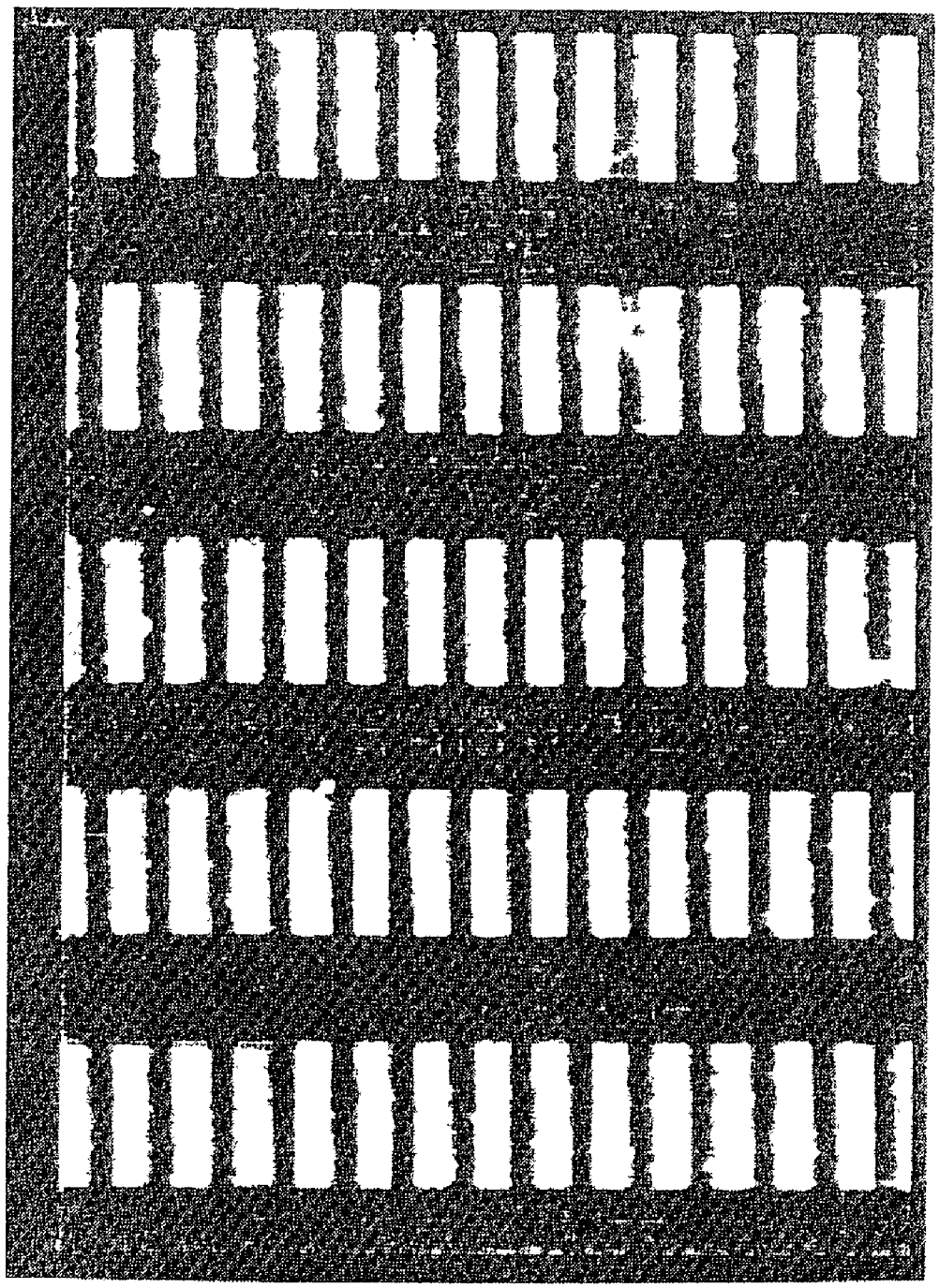
FIG. 20 is a mapping of fluorescence intensity versus location indicating fluorescein binding on 400 micron wide photolyzed regions perpendicular to 100 micron flow paths.

An image of the substrate (FIG. 20) showed regions of high fluorescence indicating that the fluorescein had bound to the substrate. White squares indicating fluorescein binding were present as 400 micron horizontal stripes on the photolyzed regions within the 100 micron vertical flow paths. Contrast ratios of 8:1 were observed between the channels and the channel spacings. This demonstrates the nearly complete physical isolation of fluid passing through 100 micron channels under 400 psi of clamping pressure.

D. Channel Matrix Hybridization Assay

A center region of a two by three inch slide was derivatized with bis(2-Hydroxyethyl) aminopropyltriethoxy silane. Six nucleosides were then coupled to the entire reaction region using a synthesis process consisting of deprotection, coupling, and oxidation steps for each monomer applied. These first six nucleosides were coupled in a reaction region defined by a 0.84 inch diameter circular well in an aluminum template clamped to the two by three inch slide.

The seventh and eighth monomers were applied to the substrate by flowing monomer solutions through 100 micron channels in an etched silicon channel block (employed in Example C above). The seventh base was coupled along the long axis (vertical) of the two-inch by three-inch slide, and the eighth base perpendicular to the seventh, along the short axis (horizontal) of the slide. This defined an active matrix region of 1.28 by 1.28 cm having a density of 2,500 reaction regions per square centimeter.

The channel block was centered over the reaction region and clamped to the substrate using a clamping assembly consisting of machined aluminum plates. This aligned the two inch by three inch substrate relative to the channel block in the desired orientation. Rotation of the top clamp plate and channel block relative to the bottom clamp plate and substrate between the seventh and eighth coupling steps provided for the matrix of intersecting rows and columns.

In the top clamp plate, fluid delivery wells were connected to laser-drilled holes which entered individual channels from the back surface of the channel block. These delivery wells were used to pipette coupling reagents into channels while the channel block was clamped to the substrate. Corresponding fluid-retrieval wells were connected to vacuum at the downstream of the channel block, drawing fluid through the channels and out to a waste container. Thus continuous fluid flow over the substrate in the channel region during coupling steps was achieved.

The complete octamer synthesized at the channel intersections formed by the seventh and eighth coupling steps had the following sequence:

Substrate—(3')CGCAGCCG(5') (SEQ. ID NO: 4).

After completion of the synthesis process, cleavage of exocyclic amines was performed by immersion of the reaction region in concentrated ammonium hydroxide. The reaction region was then incubated at 15° C. for one hour in a 10 nM solution of the complementary base sequence 5' GCGTCGGC-F (SEQ. ID No: 5), where "F" is a fluorescein molecule coupled to the 3' end of the oligonucleotide. The target chain solution was then flushed from the reaction region and replaced with neat 6×SSPE buffer, also at 15° C. Finally, the reaction region was then scanned using a laser fluorescence detection system while immersed in the buffer.

The brightest regions in the resulting image (FIG. 21) correspond to channel intersections where a full octamer was synthesized on the substrate surface. Vertical columns on the image displayed the channel regions where the seventh base was coupled, while horizontal rows display the channel regions where the eighth base was coupled. Brightness in the channel intersection regions indicated hybridization between the fluoresceinated target chain and the complementary chain synthesized and bound to the substrate in these regions. The vertical stripes of the image showed a consistent brightness with regions of significantly greater brightness at the intersection regions. The horizontal stripes did not contain the consistent brightness of the vertical stripes, but did have regions of brightness at the intersections with the vertical stripes.

The consistent brightness along the seventh monomer axis (vertical) indicated partial hybridization of the target chain in areas where seven of the eight complementary bases were coupled to the substrate surface. The lack of brightness along the eighth monomer axis (horizontal) is consistent with the expectation that a chain of six matching bases bound to the substrate surface will not hybridize effectively to an octamer in solution (heptamers with six matching bases followed by a mismatch at the seventh position). The darker background consists of hexamers consisting of the first six monomers coupled to the entire reaction region.

Figure 21:
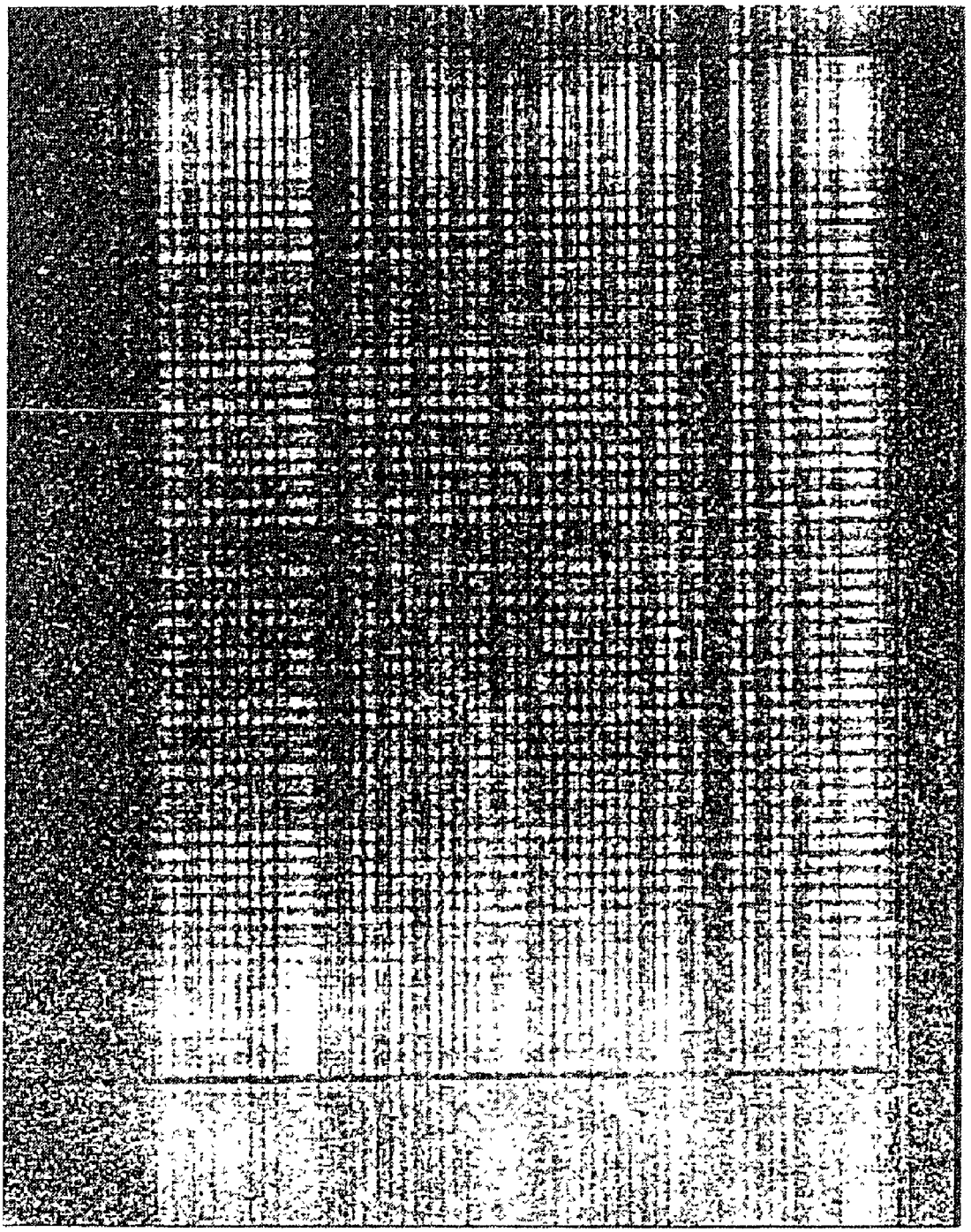
FIG. 21 is a mapping of fluorescence intensity versus location for a substrate containing octanucleotides, heptanucleotides, and hexanucleotides and incubated with an oligonucleotide complimentary to the octanucleotide.
Figure 22:
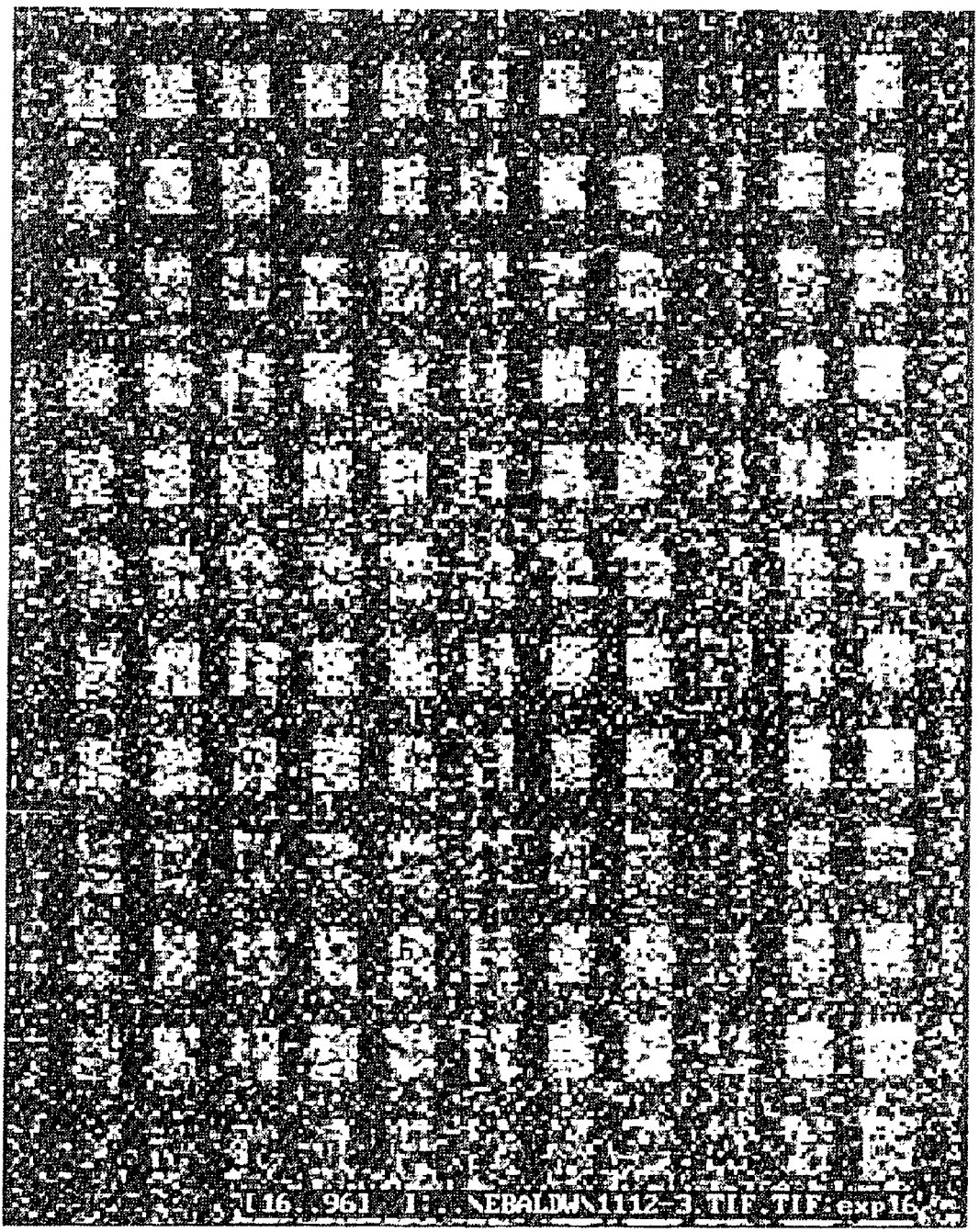
FIG. 22 is a magnified version of FIG. 21.

FIG. 22 is a magnified view of the image in FIG. 21. FIG. 22 demonstrates that the separate reaction regions are well resolved.

VII. Conclusion

The above description is illustrative and not restrictive. Many variations of the invention will become apparent to those of skill in the art upon review of this disclosure. Merely by way of example a variety of substrates, receptors, ligands, and other materials may be used without departing from the scope of the invention. The scope of the invention should, therefore, be determined not with reference to the above description, but instead should be determined with reference to the appended claims along with their full scope of equivalents.

What is claimed is:

1. A method of making an array of molecules comprising:
obtaining a substrate having a substantially flat first surface;
forming a plurality of hydrophilic reaction regions on the first surface of the substrate by:
coating the first surface of the substrate with a hydrophilic material having a plurality of reactive functional groups, wherein said plurality of reactive functional groups comprise coupled thereto a plurality of hydrophobic photo protecting groups;
activating regions where said plurality of hydrophilic reaction regions are to be located, wherein the hydrophobic photo protecting groups are removed to re-liberate the hydrophilic material with the plurality of the reactive functional groups, wherein the activated regions are surrounded by hydrophobic constraining regions comprised of intact photo protecting groups, which prevent flow of reactants from the reaction regions;
wherein the first surface includes greater than 100 reaction regions at a density of at least 1000 reaction regions/cm$^2$; and
attaching molecules to the reaction regions to form an array.

2. The method of claim 1 wherein the substrate comprises glass, pyrex, quartz, silicon, or polymer.

3. The method of claim 2 wherein the molecules are attached to the substrate using said reactive functional group.

4. The method of claim 3 wherein the reactive functional group is selected from the group consisting of an amine, a hydroxyl, a carboxyl, and a thio group.

5. The method of claim 1 wherein the molecules are selected from the group consisting of peptides, oligonucleotides, nucleic acids, and amino acids.

6. The method of claim 1 including a cover on the substrate.

7. The method of claim 1 including greater than 1000 reaction regions and a density of reaction regions being at least 1000/cm$^2$.

8. The method of claim 1 wherein the hydrophilic material is amino propyltriethoxysilane.

9. The method of claim 1 wherein the hydrophobic photo protecting groups are in the class of nitrobenzyl protection groups.

10. The method of claim 1 wherein the attaching molecules to the reaction regions to form an array includes a coupling step using a volume of solution of less than 5 nl that is contained within the hydrophilic reaction region.

* * * * *

```
                       SEQUENCE LISTING

<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: peptide made by combinatorial synthesis

<400> SEQUENCE: 1

Tyr Gly Gly Phe Leu
1               5

<210> SEQ ID NO 2
<211> LENGTH: 5
<212> TYPE: PRT
<213> ORGANISM: Artificial Sequence
<220> FEATURE:
<223> OTHER INFORMATION: peptide made by combinatorial synthesis
<220> FEATURE:
<221> NAME/KEY: MISC_FEATURE
<222> LOCATION: (2)..(2)
<223> OTHER INFORMATION: Xaa is a D amino acid

<400> SEQUENCE: 2

Tyr Xaa Gly Phe Leu
1               5

<210> SEQ ID NO 3
<211> LENGTH: 5
<212> TYPE: PRT
<213> ORGANISM: Artificial Sequence
<220> FEATURE:
<223> OTHER INFORMATION: peptide made by combinatorial synthesis
<220> FEATURE:
<221> NAME/KEY: MISC_FEATURE
<222> LOCATION: (1)..(1)
<223> OTHER INFORMATION: Xaa is a D amino acid

<400> SEQUENCE: 3

Xaa Gly Gly Phe Leu
1               5

<210> SEQ ID NO 4
<211> LENGTH: 8
<212> TYPE: DNA
<213> ORGANISM: Artificial Sequence
<220> FEATURE:
<223> OTHER INFORMATION: primer

<400> SEQUENCE: 4 gccgacgc                                                             8

<210> SEQ ID NO 5
<211> LENGTH: 8
<212> TYPE: DNA
<213> ORGANISM: Artificial Sequence
```

```
<220> FEATURE:
<223> OTHER INFORMATION: primer
<220> FEATURE:
<221> NAME/KEY: misc_feature
<222> LOCATION: (8)..(8)
<223> OTHER INFORMATION: a fluorescein molecule is coupled to the 3' end

<400> SEQUENCE: 5 gcgtcggc                                                                 8

<210> SEQ ID NO 6
<211> LENGTH: 5
<212> TYPE: PRT
<213> ORGANISM: Artificial Sequence
<220> FEATURE:
<223> OTHER INFORMATION: peptide made by combinatorial synthesis
<220> FEATURE:
<221> NAME/KEY: MISC_FEATURE
<222> LOCATION: (1)..(2)
<223> OTHER INFORMATION: Xaa is a D amino acid

<400> SEQUENCE: 6

Xaa Xaa Gly Phe Leu
1               5
```